US011471381B2

(12) United States Patent
Phillips et al.

(10) Patent No.: US 11,471,381 B2
(45) Date of Patent: Oct. 18, 2022

(54) GASTRIC JEJUNAL FEEDING TUBE DEVICES FOR GASTRIC JEJUNAL FEEDING OF AN INFANT OR CHILD

(71) Applicant: APPLIED MEDICAL TECHNOLOGY, INC., Brecksville, OH (US)

(72) Inventors: Grant Wesley Phillips, Richfield, OH (US); Derek M. Williams, Cuyahoga Falls, OH (US); George J. Picha, Brecksville, OH (US); Calia Alysia Battista, Broadview Heights, OH (US)

(73) Assignee: APPLIED MEDICAL TECHNOLOGY, INC., Brecksville, OH (US)

( * ) Notice: Subject to any disclaimer, the term of this patent is extended or adjusted under 35 U.S.C. 154(b) by 700 days.

(21) Appl. No.: 16/397,071

(22) Filed: Apr. 29, 2019

(65) Prior Publication Data
US 2019/0328621 A1    Oct. 31, 2019

Related U.S. Application Data

(60) Provisional application No. 62/664,571, filed on Apr. 30, 2018.

(51) Int. Cl.
*A61J 15/00* (2006.01)
*A61M 25/00* (2006.01)

(52) U.S. Cl.
CPC ........ *A61J 15/0069* (2013.01); *A61J 15/0015* (2013.01); *A61M 25/0043* (2013.01);
(Continued)

(58) Field of Classification Search
CPC .............. A61J 15/0069; A61J 15/0015; A61J 15/0076; A61J 15/0092; A61J 15/0073;
(Continued)

(56) References Cited

U.S. PATENT DOCUMENTS 4,668,225 A    5/1987  Russo
4,698,059 A   10/1987  Johnson
(Continued)

FOREIGN PATENT DOCUMENTS

EP    2 067 465 A2    6/2009
SU        927254 A1    5/1982

OTHER PUBLICATIONS

Innovative Products G, J and GJ-tubes with EnFit Connection, (2017) Digestive Health Product Catalogue, Halyard, pp. 6 and 9 (Year: 2017).*

(Continued)

*Primary Examiner* — James D Ponton
*Assistant Examiner* — Neeraja Gollamudi
(74) *Attorney, Agent, or Firm* — Pearne & Gordon LLP

(57) ABSTRACT

A gastric jejunal (GJ) feeding tube device for GJ feeding of an infant or child is provided. The device comprises a GJ button comprising a GJ button body, a gastric port, a jejunal port, a gastric channel, and a jejunal channel. The device also comprises a multi-lumen tube comprising a multi-lumen tube body, a multi-lumen tube proximal end, and a multi-lumen tube distal end. The device also comprises a jejunal tube comprising a jejunal tube body, a jejunal tube proximal end, a jejunal tube distal end, a spring, and a ring. The spring provides a kink-resistant feature. The ring is positioned at the jejunal tube proximal end. The jejunal tube and the GJ button are operatively connected at the ring and the mating surface by radial compression. The ring has a higher durometer than the jejunal tube body and an outer diameter that does not substantially decrease distally.

25 Claims, 21 Drawing Sheets

(52) U.S. Cl.
CPC ........ *A61J 15/0076* (2015.05); *A61J 15/0092* (2013.01); *A61M 2025/0059* (2013.01); *A61M 2210/106* (2013.01); *A61M 2240/00* (2013.01)

(58) Field of Classification Search
CPC ............ A61M 25/0043; A61M 25/005; A61M 25/0052; A61M 2025/0059; A61M 2240/00
See application file for complete search history.

(56) References Cited

U.S. PATENT DOCUMENTS

| | | | |
|---|---|---|---|
| 5,527,280 A | 6/1996 | Goelz | |
| 5,665,064 A * | 9/1997 | Bodicky | A61J 15/0007 600/156 |
| 5,879,499 A | 3/1999 | Corvi | |
| 6,077,243 A | 6/2000 | Quinn | |
| 6,623,490 B1 | 9/2003 | Crane et al. | |
| 9,302,090 B2 | 4/2016 | Williams et al. | |
| 9,539,181 B2 | 1/2017 | Phillips et al. | |
| 2005/0033267 A1 * | 2/2005 | Decaria | A61M 39/12 604/533 |
| 2005/0197624 A1 | 9/2005 | Goodson, IV et al. | |
| 2005/0222581 A1 | 10/2005 | Fischer et al. | |
| 2007/0100295 A1 * | 5/2007 | Belley | A61M 39/06 604/246 |
| 2007/0162108 A1 | 7/2007 | Carlson | |
| 2008/0108974 A1 | 5/2008 | Yee Roth | |
| 2008/0140055 A1 | 6/2008 | Shirley | |
| 2009/0149834 A1 | 6/2009 | Moss | |
| 2009/0221960 A1 * | 9/2009 | Albrecht | A61B 17/3421 604/103.03 |
| 2009/0281500 A1 | 11/2009 | Acosta et al. | |
| 2010/0036365 A1 | 2/2010 | Becker | |
| 2012/0203171 A1 * | 8/2012 | Williams | A61J 15/0069 604/96.01 |
| 2014/0024955 A1 | 1/2014 | Zhadkevich | |
| 2014/0031755 A1 | 1/2014 | Williams et al. | |
| 2014/0194823 A1 * | 7/2014 | Phillips | A61M 25/005 604/175 |

OTHER PUBLICATIONS

Beswick Engineering, "The Basics of Compression Fittings," May 21, 2019, available at https://www.beswick.com/resources/the-basics-of-compression-fittings/ (select "Free Download"), last accessed Mar. 4, 2022, pp. 1-5.

* cited by examiner

GASTRIC JEJUNAL FEEDING TUBE DEVICES FOR GASTRIC JEJUNAL FEEDING OF AN INFANT OR CHILD

CROSS-REFERENCE TO RELATED APPLICATIONS

This application claims benefit of U.S. Provisional Application 62/664,571, filed Apr. 30, 2018, the entire disclosure of which is hereby incorporated herein by reference.

FIELD OF THE INVENTION

The invention relates generally to a gastric jejunal (GJ) feeding tube device for GJ feeding of an infant or child, and more particularly to such a device comprising (a) a GJ button comprising a GJ button body, a gastric port, a jejunal port, a gastric channel, and a jejunal channel, (b) a multi-lumen tube comprising a multi-lumen tube body, a multi-lumen tube proximal end, and a multi-lumen tube distal end, and (c) a jejunal tube comprising a jejunal tube body, a jejunal tube proximal end, a jejunal tube distal end, a spring, and a ring.

BACKGROUND OF THE INVENTION

Low profile gastric jejunal (GJ) feeding tubes devices have been developed for use in smaller patients, such as pediatric patients, in small sizes such as 14 French. Use of GJ feeding tube devices for infants and children presents challenges based on the small size of the corresponding intestinal anatomy. For example, the jejunal portion of the small intestine in infants is tight, compact, and tortuous. The entire gastrointestinal tract fits in an abdominal cavity roughly the size of a softball. Each twist and turn of the jejunum must be navigated by the distal portion of the GJ feeding tube device.

The probability that a feeding tube of a GJ feeding tube device will kink increases with increasing tortuousness of a jejunal path. Kinking involves restricting flow through a feeding tube, either partially or entirely. If a feeding tube kinks, the GJ feeding tube device is rendered ineffective and must be replaced. Most patients that depend upon direct jejunal feedings for nutrition cannot tolerate a kinked feeding tube for long. Since most placements of GJ feeding tube devices are performed by interventional radiology, the reoccurrence of this expensive procedure is something that hospitals and insurance companies would like to limit. Parents of pediatric patients also would like to reduce time that their children have to spend at hospitals for placements, and amounts of exposure to radiation that their children receive during placements.

Miniaturization of GJ feeding tube devices for use in infants and children presents challenges with respect to providing products that are safe and effective for GJ feeding, including with respect to avoiding kinks of feeding tubes of the devices, without the products being unduly obtrusive or causing discomfort. This is particularly so for GJ feeding tube devices made of multiple parts that must be operatively connected, e.g. GJ button devices including GJ buttons, ports, and tubes, for which the parts are made from materials that may not be easily adhered to each other with respect to small surface areas, e.g. silicone and polyurethane, and that include narrow internal cavities, e.g. channels, lumens, and passages, through which liquid compositions, e.g. nutrient compositions and pharmaceutical compositions, must be able to flow.

For example, Moss et al., U.S. Pub. No. 2009/0149834, discloses an enteral feeding catheter that includes inner and outer layers of tubes and a spring positioned between them. The inner and outer tubes are coupled together so that the spring is held between them. In some embodiments, the enteral feeding catheter includes a connector connected to a proximal portion of the enteral feeding catheter. The connector allows the enteral feeding catheter to be connected to a machine, such as a feeding or suction machine. Unfortunately, Moss does not disclose details of the connector. Moss also does not disclose joining the enteral feeding catheter to other tubes of GJ feeding tube devices placed in a patient. Moss also does not disclose use of the enteral feeding catheter with infants or children.

Phillips et al., U.S. Pat. No. 9,539,181, discloses tubing for use in gastrointestinal applications that includes a hollow tube and a spring positioned inside the tube. The spring is corrosion resistant and helps to prevent kinking of the tubing when the tubing is bent. In some embodiments the kink-resistant tubing is for use with a multi-lumen feeding tube. The multi-lumen proximal portion of the tubing is formed using an extrusion or other process. A GJ button is overmolded over the tubing at a proximal end of the tubing. Also included is a separately molded jejunal tube that may optionally include a cone-shaped proximal portion. The spring can be coextruded with the tubing during the tubing manufacturing process such that the spring is embedded into the wall of the tubing. The spring can extend from the proximal end to the distal end of the tubing. The cone-shaped portion may be formed during the extrusion process, or may be overmolded onto the proximal end of the tubing in a post-processing step. The cone-shaped portion can be a different material than the tubing and may have a higher durometer. This can provide a slightly stiffer cone-shaped portion so that the cone-shaped portion can more readily mate with an interior surface of the GJ button. The jejunal tube can be positioned inside an existing multi-lumen feeding tube and GJ button. The jejunal tube can be inserted into the jejunal opening of the GJ button and pressed into the jejunal opening until the cone-shaped portion of the tube seats into a similarly shaped cone-shaped portion inside the jejunal opening of the GJ button. Unfortunately, the extent to which this configuration is amendable to miniaturization is not clear.

Accordingly, a need exists for improved GJ feeding tube devices for GJ feeding of an infant or child.

BRIEF SUMMARY OF THE INVENTION

A gastric jejunal (GJ) feeding tube device for GJ feeding of an infant or child is disclosed.

The GJ feeding tube device comprises a GJ button comprising (i) a GJ button body, (ii) a gastric port, (iii) a jejunal port, (iv) a gastric channel, and (v) a jejunal channel. The GJ button body has a proximal surface, a distal surface, and a base opening. The gastric port and the jejunal port are positioned at the proximal surface. The base opening is positioned at the distal surface. The gastric channel and the jejunal channel extend from the gastric port and the jejunal port, respectively, to the base opening. The jejunal channel has a mating surface therein.

The GJ feeding tube device also comprises a multi-lumen tube comprising (i) a multi-lumen tube body, (ii) a multi-lumen tube proximal end, and (iii) a multi-lumen tube distal end. The multi-lumen tube body defines a gastric lumen and a jejunal lumen. The gastric lumen and the jejunal lumen each have a proximal opening located at the multi-lumen tube proximal end and a distal opening located along the multi-lumen tube body or at the multi-lumen tube distal end.

The GJ feeding tube device also comprises a jejunal tube comprising (i) a jejunal tube body, (ii) a jejunal tube proximal end, (iii) a jejunal tube distal end, (iv) a spring, and (v) a ring. The jejunal tube body defines a jejunal tube passage having a proximal opening located at the jejunal tube proximal end and a distal opening located at the jejunal tube distal end. The spring is positioned within the jejunal tube body, extends therealong, and provides a kink-resistant feature thereto. The ring is positioned at the jejunal tube proximal end, coaxially with respect to the jejunal tube body.

The jejunal tube and the GJ button are operatively connected at the ring and the mating surface. The mating surface radially compresses the ring.

The multi-lumen tube and the GJ button are operatively connected at the multi-lumen tube proximal end and the base opening. The jejunal tube extends through the jejunal lumen of the multi-lumen tube.

The ring has a higher durometer than the jejunal tube body. The ring has an outer diameter that does not substantially decrease distally with respect to the jejunal tube.

BRIEF DESCRIPTION OF THE DRAWINGS

These and other features, aspects, and advantages of the present disclosure are better understood when the following detailed description is read with reference to the accompanying drawings, in which.

and

Figure 1:
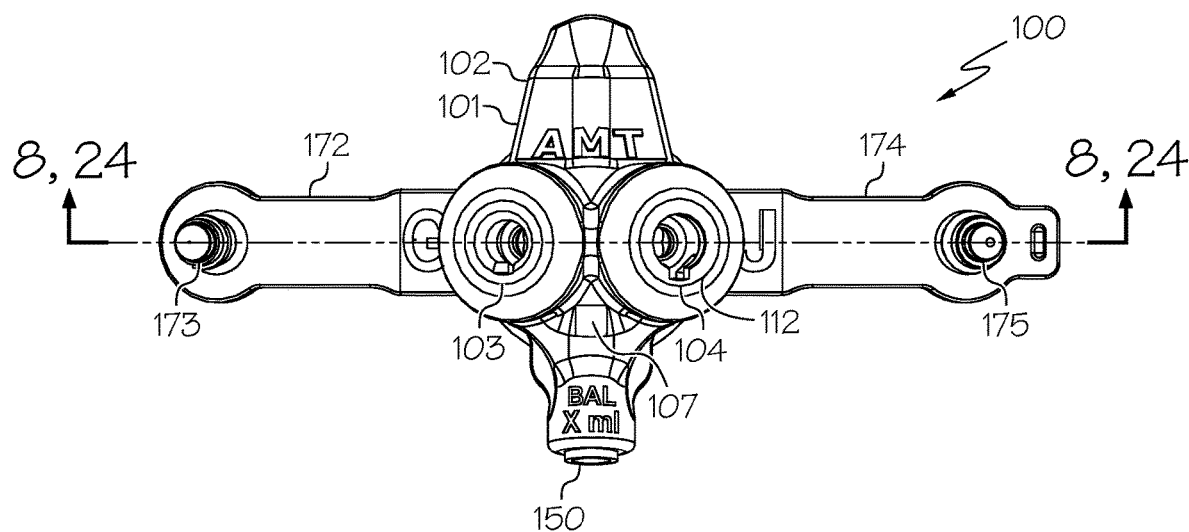
FIG. 1 is a top view of an exemplary GJ feeding tube device, including a balloon, the balloon being inflated, as disclosed herein.
Figure 2:
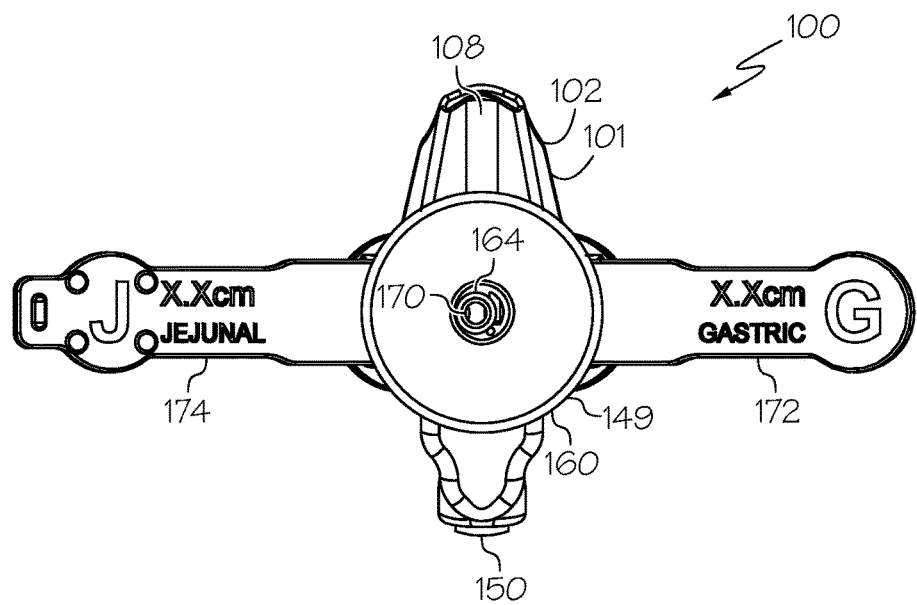
FIG. 2 is a bottom view of the GJ feeding tube device of FIG. 1.
Figure 27:
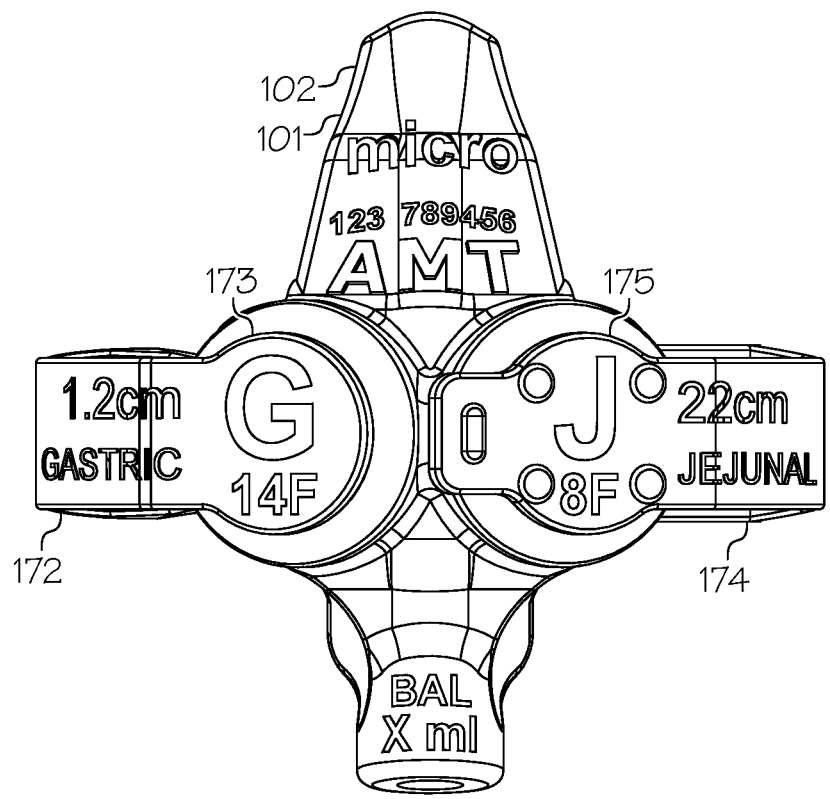

FIG. 27 is a top view of the GJ button of the GJ feeding tube device of FIG. 1, shown separately from the GJ feeding tube device, with the gastric port plug and the jejunal port plug inserted in the GJ button at the gastric port and the jejunal port, respectively.

DETAILED DESCRIPTION

As noted above, a gastric jejunal (GJ) feeding tube device for GJ feeding of an infant or child is disclosed. The GJ feeding tube device provides advantages, including that a jejunal tube of the device can be joined securely to a GJ button of the device, despite miniaturization of the GJ feeding tube device for use in infants and children, based on mating of a ring positioned at a proximal end of the jejunal tube and a mating surface located within a jejunal channel of the GJ button. The jejunal tube and the GJ button are operatively connected at the ring and the mating surface. Also, the mating surface radially compresses the ring. The ring has a higher durometer than the jejunal tube body. Also, the ring has an outer diameter that does not substantially decrease distally with respect to the jejunal tube.

Without wishing to be bound by theory, it is believed that this configuration results in a secure joint that is particularly suitable for GJ buttons and jejunal tubes comprising soft, flexible materials, such as silicone and polyurethane, that are dimensioned to be sufficiently small for use in infants and children, for example based on use of jejunal tubes of sizes French 8 or smaller. Because the ring has a higher durometer than the jejunal tube body and the outer diameter of the ring does not substantially decrease distally with respect to the jejunal tube, the ring can be made sufficiently small to fit within a jejunal channel of the GJ button, without being deformed in a way so as to block the jejunal channel. Moreover, the ring can substantially maintain its shape when the jejunal tube is being pulled distally with respect to the GJ button, e.g. during assembly. This allows the ring to mate with the mating surface, thereby properly positioning the jejunal tube with respect to the GJ button. This also allows the ring to remain mated with the mating surface during use, thereby maintaining the operative connection of the jejunal tube and the GJ button.

Advantages include that physicians can place the GJ feeding tube devices, now including jejunal tubes of sizes of French 8 or smaller, in patients corresponding to infants and/or children, with less extensive dilation of the pyloric sphincter than has been needed for tubes of larger sizes, e.g. French 12 or greater. For placement of jejunal tubes, physicians dilate the pyloric sphincter of a patient in order to allow the distal end of the jejunal tube to pass from the stomach to the small intestine. Following placement, the pyloric sphincter remains dilated during the weeks or months that the device remains in the patient. Less extensive dilation should allow the pyloric sphincter to close more readily, and resume normal function more rapidly, once use of the device is complete and the device is removed.

Also, the GJ feeding tube devices allow for use of jejunal tubes that are sized appropriately for infants and children, based on the jejunal tubes having outer diameters that are smaller than the inner diameters of the small intestines of infants and children, and that are appropriately flexible, based on being more flexible than the small intestines. The use of jejunal tubes that are sized appropriately should promote absorbance of nutrients. Appropriate flexibility should decrease the risk of injury.

Accordingly, the GJ feeding tube device for GJ feeding of an infant or child can be used for GJ feeding of patients generally, e.g. including adults, and can be used particularly advantageously for GJ feeding of patients have a small intestinal anatomy, e.g. particularly infants and children. Thus, the GJ feeding tube devices can be safe and effective, while also being reasonably comfortable for patients, and this is particularly so for patients corresponding to infants and/or children.

Considering the GJ feeding tube device in detail, as shown in FIGS. 1-9, the GJ feeding tube device 100 comprises a GJ button 101 comprising (i) a GJ button body 102, (ii) a gastric port 103, (iii) a jejunal port 104, (iv) a gastric channel 105, and (v) a jejunal channel 106. The GJ button 101 is an external bolster for the GJ feeding tube device 100. The GJ button 101 remains external to a patient, e.g. an infant or child in need of the GJ feeding tube device 100, following placement of the GJ feeding tube device 100 in the patient. The GJ button 101 is dimensioned to prevent the GJ button 101 from slipping into the patient following placement, e.g. the GJ button body 102 is substantially wider than an incision in the abdomen of the patient through which the GJ button 101 is placed, thereby preventing the GJ button 101 from slipping into the patient following placement.

In some examples, the GJ button 101 also is dimensioned to have a low-profile with respect to skin of the patient through which the GJ feeding tube device 100 has been placed in the patient. This prevents the GJ feeding tube device 100 from being unduly obtrusive and promotes comfort for the patient.

As shown in FIGS. 1-5 and FIG. 10, the GJ button body 102 has a proximal surface 107, a distal surface 108, and a base opening 109. The GJ button body 102 can have an irregular shape, reflective of the presence of multiple ports and channels. The proximal surface 107 can comprise one or more surfaces of the GJ button body 102 that remain readily accessible to a physician following placement in a patient, e.g. based on the proximal surface 107 not facing the patient. The distal surface 108 can comprise one or more surfaces of the GJ button body 102 that do not remain readily accessible, e.g. based on the distal surface 108 facing the patient.

The GJ button body 102 can comprise one or more soft polymeric materials, such as one or more of silicone or polyurethane, among other materials. In some examples, the GJ button body 102 is made from silicone, e.g. 90%, 95%, 99%, or 100% of the material of the GJ button body 102 is silicone. In some examples, the GJ button body 102 is made from polyurethane, e.g. 90%, 95%, 99%, or 100% of the material of the GJ button body 102 is polyurethane.

As shown in FIGS. 1-5, FIG. 9, and FIG. 10, the gastric port 103 and the jejunal port 104 are positioned at the proximal surface 107 of the GJ button body 102. The base opening 109 is positioned at the distal surface 108. The gastric channel 105 and the jejunal channel 106 extend from the gastric port 103 and the jejunal port 104, respectively, to the base opening 109. Based on this configuration, a gastric connector can be connected to the gastric port 103 for delivery of liquid compositions, e.g. nutrient compositions, pharmaceutical compositions, etc., from tubing, via the gastric connector, to the gastric port 103 and the gastric channel 105. Likewise, a jejunal connector can be connected to the jejunal port 104 for delivery of liquid compositions, e.g. nutrient compositions, pharmaceutical compositions, etc., from tubing, via the jejunal connector, to the jejunal port 104 and the jejunal channel 106.

Figure 9:
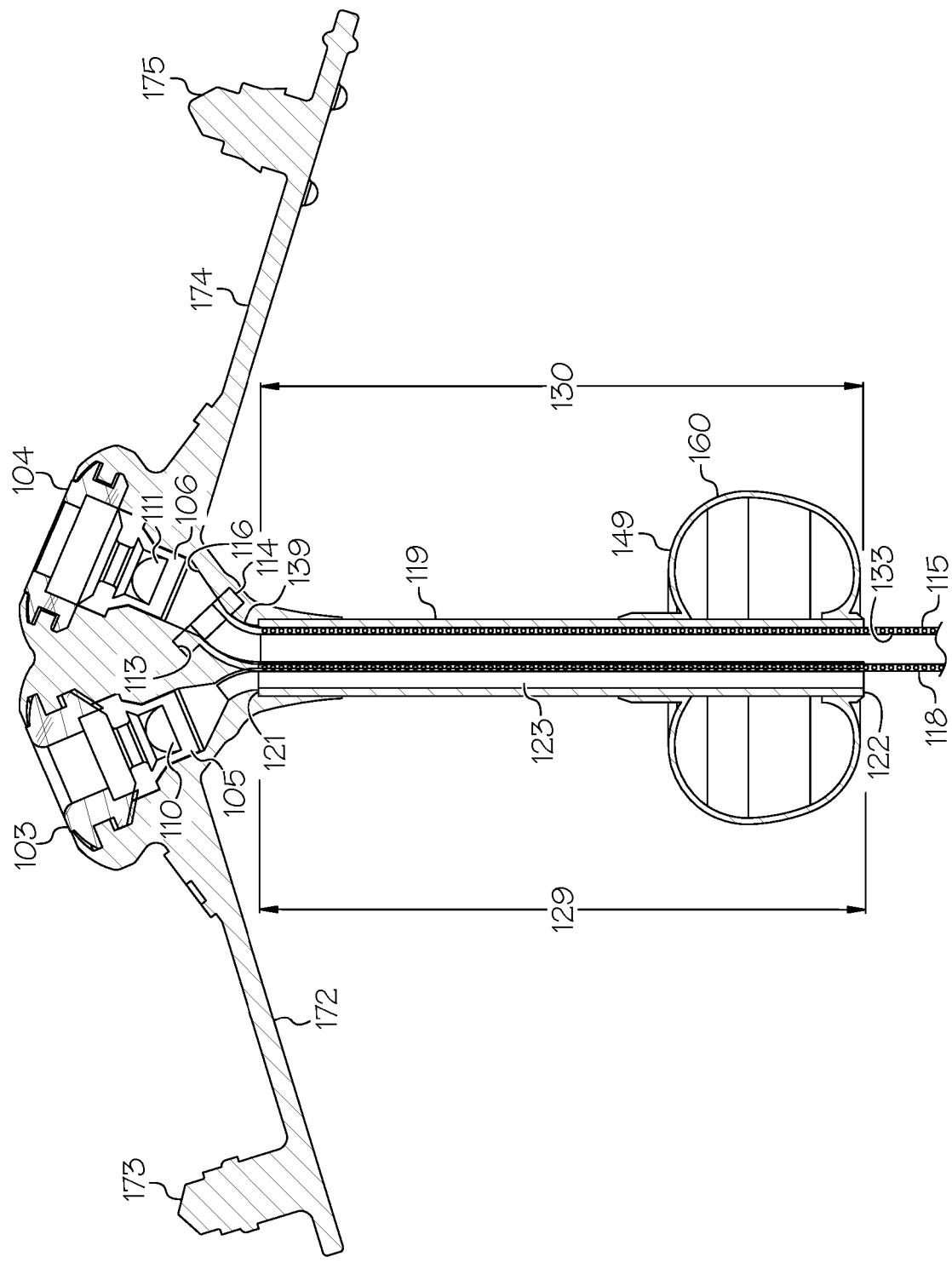
FIG. 9 is an enlarged view of the sectional view of the GJ button, the multi-lumen tube, and the balloon of the GJ feeding tube device as shown FIG. 8.
Figure 10:
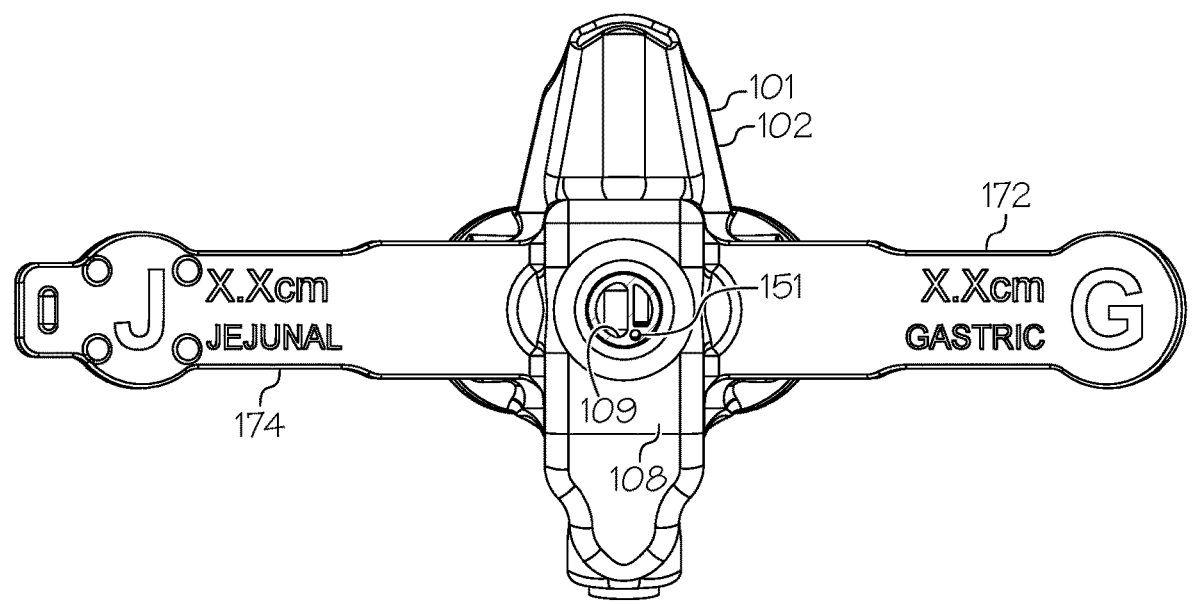
FIG. 10 is a bottom view of the GJ button of the GJ feeding tube device of FIG. 1, shown separately from the GJ feeding tube device.

As shown in FIG. 9, in some examples, one or both of the gastric port 103 or the jejunal port 104 comprise a gastric port valve 110 or a jejunal port valve 111, respectively. This can allow control of flow of liquid compositions through the gastric port 103 and/or the jejunal port 104. In some examples the gastric port valve 110 and/or jejunal port valve 111 is a check valve, such as a duck-bill valve. This can allow control of flow of liquid compositions one-way through the gastric port 103 and/or the jejunal port 104, such that the liquid compositions can flow distally, to the patient, but not proximally, from the patient. This can prevent backflow of fluids, e.g. liquids and gases, from the stomach and/or small intestine of a patient, through the gastric port 103 and/or the jejunal port 104.

As shown in FIG. 1 and FIG. 9, in some examples, one or both of the gastric port 103 or the jejunal port 104 comprise a photoluminescent portion 112. For example, the jejunal port 104 can comprise a photoluminescent portion 112, while the gastric port 103 does not. This can allow caregivers to distinguish the gastric port 103 and the jejunal port 104, e.g. when connecting and disconnecting connectors and tubing for feeding, under low light conditions, e.g. without turning on lights in a hospital room. This is advantageous for infants and children who are receiving nutrition through a jejunal port 104, as these infants and children generally will need to be connected to a feeding pump during most of each day and night. This makes it easier for caregivers to change connections without waking the infants or children.

As shown in FIG. 9, the jejunal channel 106 has a mating surface 113 therein. The mating surface 113 is for mating with a ring 114 of a jejunal tube 115, as discussed below.

Figure 18:
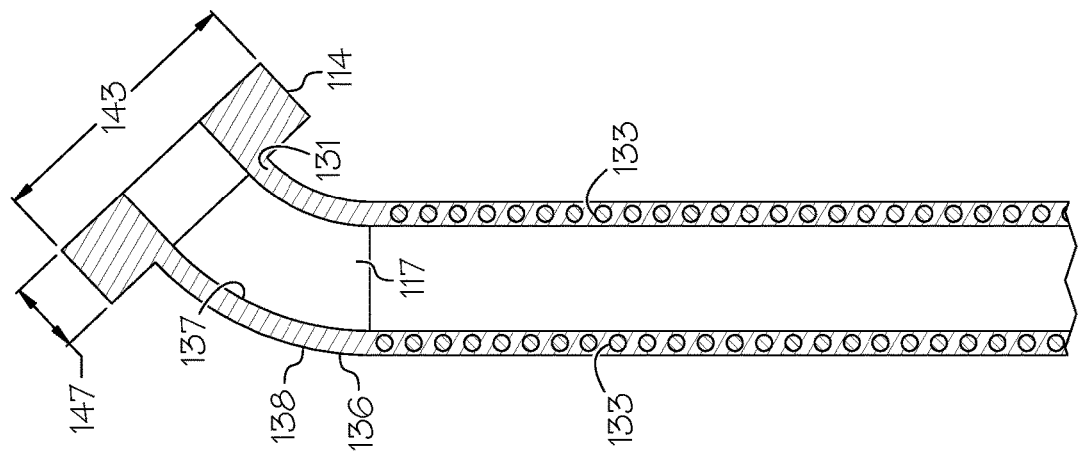
FIG. 18 is an enlarged sectional view of a proximal portion of the jejunal tube of the GJ feeding tube device as shown FIG. 8.
Figure 17:
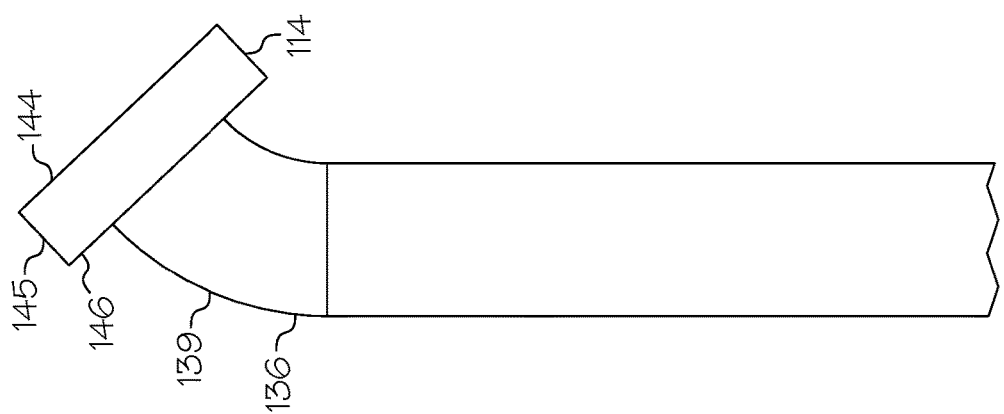
FIG. 17 is an enlarged first side view of a proximal portion of the jejunal tube of the GJ feeding tube device of FIG. 1, shown separately from the GJ feeding tube device.
Figure 20:
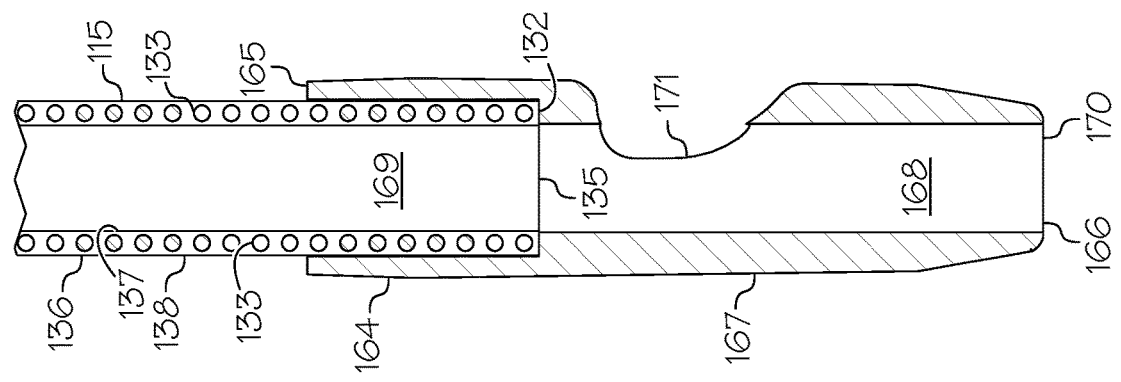
FIG. 20 is an enlarged sectional view of a distal portion of the jejunal tube of the GJ feeding tube device as shown FIG. 8.

Again with reference to FIG. 9, in some examples, the jejunal channel 106 further comprises a funnel portion 116 between the jejunal port 104 and the mating surface 113, the funnel portion 116 having an inner diameter that decreases distally. In accordance with these examples, the funnel portion 116 can serve to decrease the inner diameter of the jejunal channel 106, from a larger proximal inner diameter at the jejunal port 104, to a smaller distal inner diameter at the mating surface 113. With reference to FIG. 9 and FIG. 18, this can help to prevent leakage of liquid compositions, e.g. nutrient compositions and/or pharmaceutical compositions, from the GJ button 101, as the liquid compositions flow from jejunal channel 106 of the GJ button 101 to the jejunal tube passage 117 of the jejunal tube body 118, as discussed below.

Figure 3:
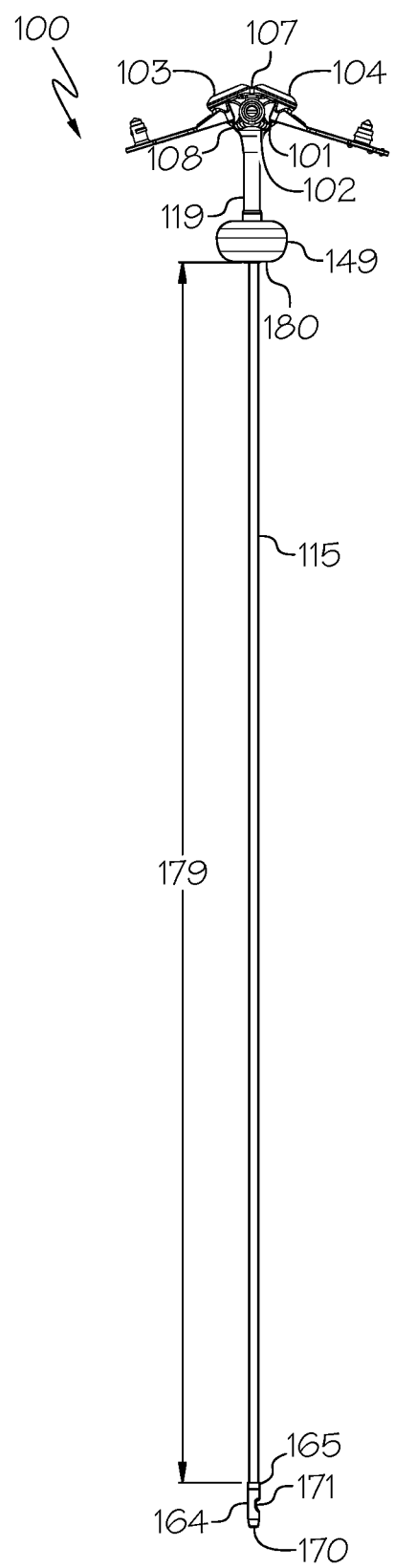
FIG. 3 is a first side view of the GJ feeding tube device of FIG. 1.
Figure 4:
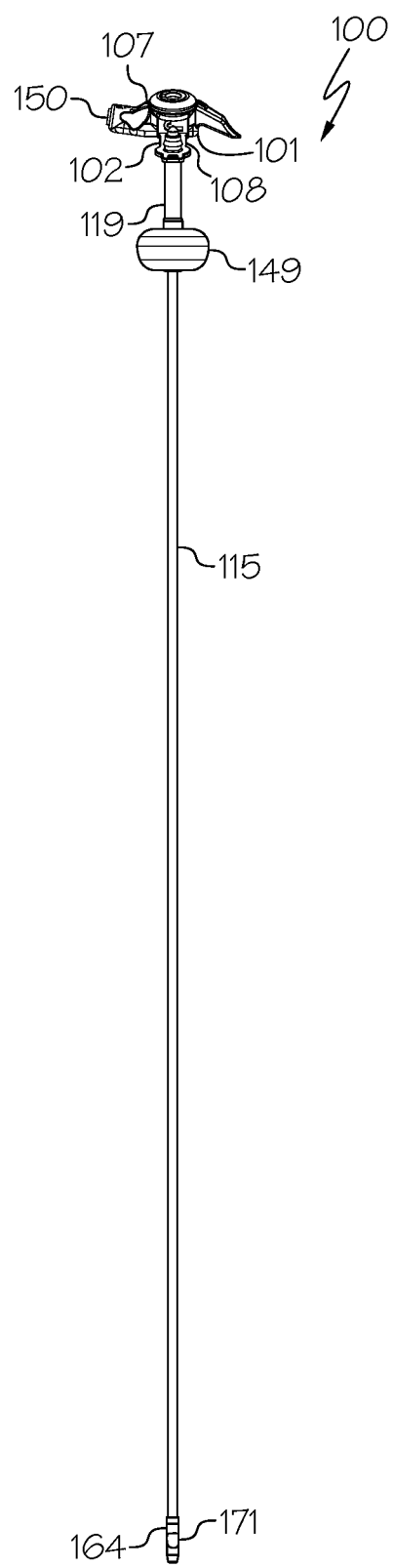
FIG. 4 is a second side view of the GJ feeding tube device of FIG. 1.

As shown in FIG. 3 and FIG. 9, the GJ feeding tube device 100 also comprises a multi-lumen tube 119 comprising (i) a multi-lumen tube body 120, (ii) a multi-lumen tube proximal end 121, and (iii) a multi-lumen tube distal end 122.

As shown in FIG. 9 and FIGS. 11-13, the multi-lumen tube body 120 defines a gastric lumen 123 and a jejunal lumen 124. The gastric lumen 123 and the jejunal lumen 124 each have a proximal opening, i.e. a gastric lumen proximal opening 125 and a jejunal lumen proximal opening 126, respectively, located at the multi-lumen tube proximal end 121 and a distal opening, i.e. a gastric lumen distal opening 127 and a jejunal lumen distal opening 128, respectively, located along the multi-lumen tube body 120 or at the multi-lumen tube distal end 122. Based on this configuration, following placement of the GJ feeding tube device 100 in a patient, the multi-lumen tube body 120 can hold the jejunal tube 115 adjacent the gastric lumen 123 within the stomach of the patient, as will become apparent below.

In some examples, the multi-lumen tube body 120 has a size of French 14 or smaller. Thus, in some examples the multi-lumen tube body 120 has a size of French 14. Also in some examples the multi-lumen tube body 120 has a size of French 12. Also in some examples the multi-lumen tube body 120 has a size of French 10. Also in some examples the multi-lumen tube body 120 has a size intermediate between French 14 and French 10, that is less than French 10, and/or that is French 14 or less and that varies, among other sizes.

With reference to FIG. 9, in some examples, the gastric lumen 123 of the multi-lumen tube 119 has a gastric lumen length 129, the jejunal lumen 124 of the multi-lumen tube 119 has a jejunal lumen length 130, and the gastric lumen length 129 is about the same as the jejunal lumen length 130. Thus, in some examples the gastric lumen length 129 and the jejunal lumen length 130 can differ from each other by less than 10%, less than 5%, or less than 1%. Also, in some examples the gastric lumen length 129 can be the same as the jejunal lumen length 130.

The multi-lumen tube body 120 can comprise one or more soft polymeric materials, such as one or more of silicone or polyurethane, among other materials. In some examples, the multi-lumen tube body 120 is made from silicone, e.g. 90%, 95%, 99%, or 100% of the material of the multi-lumen tube body 120 is silicone. In some examples, the multi-lumen tube body 120 is made from polyurethane, e.g. 90%, 95%, 99%, or 100% of the material of the multi-lumen tube body 120 is polyurethane.

As shown in FIG. 3, FIG. 9, and FIGS. 14-20, the GJ feeding tube device 100 also comprises a jejunal tube 115 comprising (i) a jejunal tube body 118, (ii) a jejunal tube proximal end 131, (iii) a jejunal tube distal end 132, (iv) a spring 133, and (v) a ring 114.

The jejunal tube body 118 defines a jejunal tube passage 117 having a proximal opening 134 located at the jejunal tube proximal end 131 and a distal opening 135 located at the jejunal tube distal end 132.

The jejunal tube body 118 has a size of French 8 or smaller. Thus, in some examples the jejunal tube body 118 has a size of French 8. Also in some examples the jejunal tube body 118 has a size of French 6. Also in some examples the jejunal tube body 118 has a size intermediate between French 8 and French 6, a size that is less than French 6, and/or a size that is French 8 or less and that varies, among other sizes.

The jejunal tube body 118 can comprise one or more polymeric materials, such as one or more of polyurethane or silicone, among other materials. In some examples, the jejunal tube body 118 is made from polyurethane, e.g. 90%, 95%, 99%, or 100% of the material of the jejunal tube body 118 is polyurethane. In some examples, the jejunal tube body 118 is made from silicone, e.g. 90%, 95%, 99%, or 100% of the material of the jejunal tube body 118 is silicone.

As shown in FIG. 9 and FIGS. 14-20, the spring 133 is positioned within the jejunal tube body 118, extends therealong, and provides a kink-resistant feature thereto. The spring 133 can be positioned within the jejunal tube body 118 in various ways. In some examples the jejunal tube body 118 comprises a jejunal tube body wall 136, the spring 133 being embedded in the jejunal tube body wall 136. This can be accomplished, for example, by positioning the spring 133 in the jejunal tube body wall 136 during extrusion of the jejunal tube body 118. In some of these examples, the jejunal tube body wall 136 comprises an inner wall 137 and an outer wall 138, the spring 133 being positioned between the inner wall 137 and the outer wall 138. Also, in some examples the jejunal tube body 118 comprises a jejunal tube body wall 136, the spring 133 being encapsulated on an inner surface of the jejunal tube body wall 136. This can be accomplished, for example, by positioning the spring 133 within the jejunal tube passage 117 after extrusion of the jejunal tube body 118, and encapsulating the spring 133.

Again with reference to FIG. 9 and FIGS. 14-20, the spring 133 can extend along part or all of the length of the jejunal tube body 118. In some examples the spring 133 extends from near the jejunal tube proximal end 131 to the jejunal tube distal end 132, such that the spring 133 extends along most, but not all, of the length of the jejunal tube body 118, e.g. about 90% to 98% of the length. In some of these examples the jejunal tube body 118 comprises a curved segment 139 between the proximal end of the jejunal tube body 118 and the spring 133. Also, in some examples the spring 133 extends from the jejunal tube proximal end 131 to the jejunal tube distal end 132, such that spring 133 extends along all of the length of the jejunal tube body 118.

The spring 133 can provide the kink-resistant feature to the jejunal tube body 118, helping the jejunal tube body 118 to maintain patency and flow therethrough despite bends, twists, and turns of the jejunal tube body 118 through folds of the small intestine of a patient. Advantageously, even when the jejunal tube body 118 is tightly pinched, the spring 133 can prevent kinks.

The spring 133 can comprise one or more of a flexible polymer or a biocompatible metal, among other materials. A spring 133 made from a flexible polymer can be useful for making the GJ feeding tube device 100 MRI-safe based on being free of metal. A spring 133 made from a biocompatible metal can be radiopaque, allowing a physician to easily view the placement by X-ray. Thus, in some examples the spring 133 can comprise one or more of polyether ether ketone, stainless steel, nylon, or high density polyethylene, among other materials. In some examples, the spring 133 is made from polyether ether ketone, e.g. 90%, 95%, 99%, or 100% of the material of the spring 133 is polyether ether ketone. In some examples, the spring 133 is made from stainless steel, e.g. 90%, 95%, 99%, or 100% of the material of the spring 133 is stainless steel. In some examples, the spring 133 is made from nylon, e.g. 90%, 95%, 99%, or 100% of the material of the spring 133 is nylon. In some examples, the spring 133 is made from high density polyethylene, e.g. 90%, 95%, 99%, or 100% of the material of the spring 133 is high density polyethylene.

As shown in FIGS. 14-20, the ring 114 is positioned at the jejunal tube proximal end 131, coaxially with respect to the jejunal tube body 118. This positioning maintains the proximal opening 134 of the jejunal tube passage 117. This positioning can be accomplished, for example, by overmolding or use of adhesives, among other approaches. Thus, in some examples the ring 114 is positioned at the jejunal tube proximal end 131 based on overmolding the jejunal tube body 118 with the ring 114. The ring 114 can have a generally solid, e.g. filled, toroidal structure about the proximal opening 134.

The ring 114 can comprise one or more of polyurethane or high-durometer silicone, among other materials. In some examples, the ring 114 is made from polyurethane, e.g. 90%, 95%, 99%, or 100% of the material of the ring 114 is polyurethane. In some examples, the ring 114 is made from high-durometer silicone, e.g. 90%, 95%, 99%, or 100% of the material of the ring 114 is high-durometer silicone.

Figure 24:
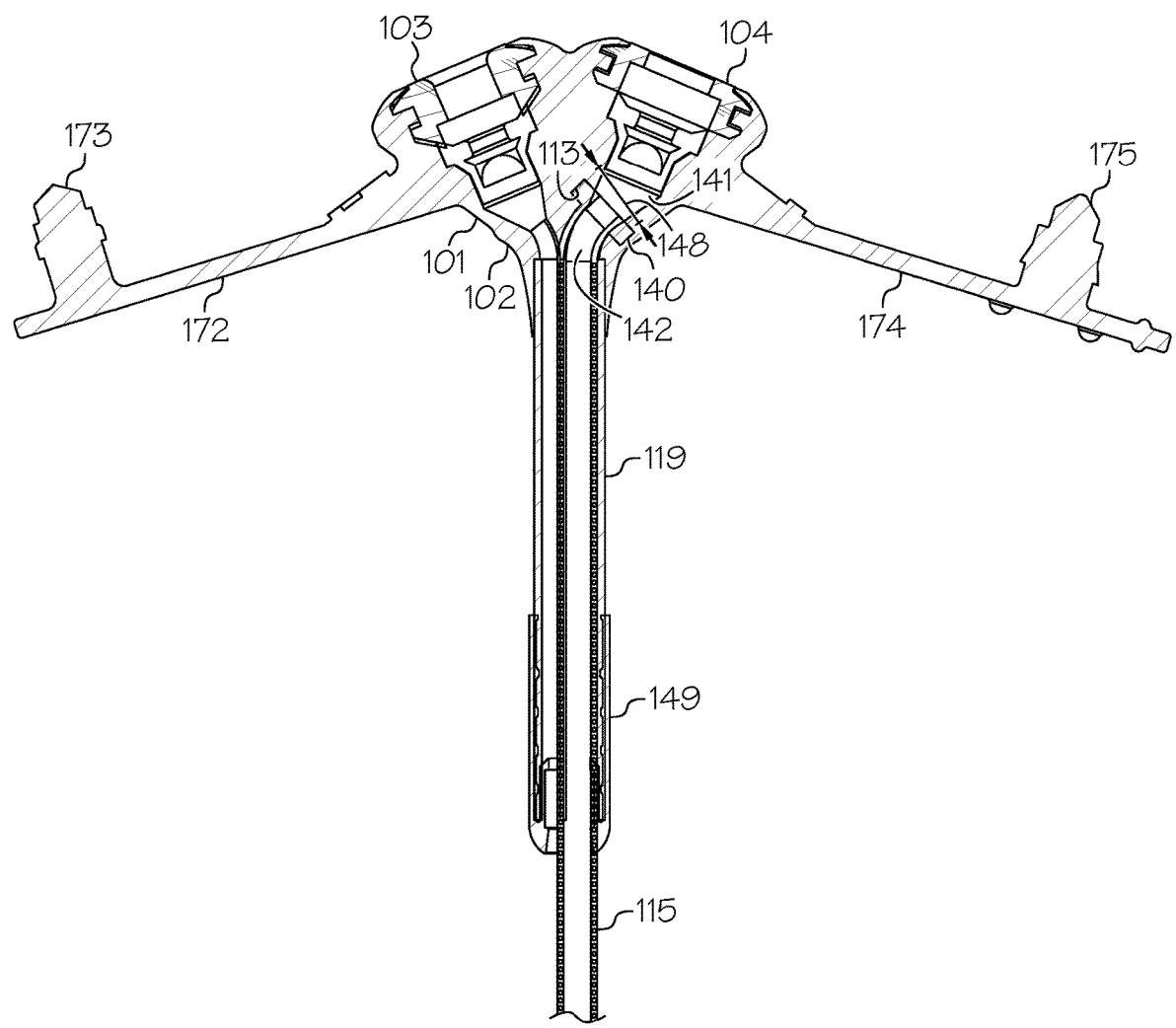
FIG. 24 is an enlarged sectional view of the GJ button, the multi-lumen tube, and the balloon of the GJ feeding tube device of FIG. 1, the balloon being deflated.

As shown in FIG. 9 and FIG. 24, the jejunal tube 115 and the GJ button 101 are operatively connected at the ring 114 and the mating surface 113. The mating surface 113 radially compresses the ring 114.

As noted above, the jejunal channel 106 has a mating surface 113 therein, and the mating surface 113 is for mating with the ring 114 of the jejunal tube 115. For example, the jejunal channel 106 can include a void 140 having an inner diameter greater than that of jejunal channel portions 141, 142 of the jejunal channel 106 immediately proximal and distal to the void 140. The mating surface 113 can be an inner surface of the void 140. The ring 114 can fit into the void 140, such that the ring 114 and the mating surface 113 come into contact, thereby mating. The ring 114 also can be held in place, based on the mating surface 113 radially compressing the ring 114, such that the ring 114 and the mating surface 113 remain mated.

With reference to FIG. 9, FIGS. 16-18, and FIG. 24, the ring 114 has a higher durometer than the jejunal tube body 118. Also, the ring 114 has an outer diameter 143 that does not substantially decrease distally with respect to the jejunal tube 115. As noted above, because the ring 114 has a higher durometer than the jejunal tube body 118 and the outer diameter 143 of the ring 114 does not substantially decrease distally with respect to the jejunal tube 115, the ring 114 can be made sufficiently small to fit within a jejunal channel 106 of the GJ button 101, without being deformed in a way so as to block the jejunal channel 106. Moreover, the ring 114 can substantially retain its shape when the jejunal tube 115 is being pulled distally with respect to the GJ button 101. This allows the ring 114 to mate with the mating surface 113, thereby properly positioning the jejunal tube 115 with respect to the GJ button 101. This also allows the ring 114 to remain mated with the mating surface 113 during use, thereby maintaining the operative connection of the jejunal tube 115 and the GJ button 101.

Again with reference to FIG. 9, FIGS. 16-18, and FIG. 24, as noted above, in some examples the jejunal channel 106 further comprises a funnel portion 116 between the jejunal port 104 and the mating surface 113, the funnel portion 116 having an inner diameter that decreases distally. As also noted, the funnel portion 116 can serve to decrease the inner diameter of the jejunal channel 106, from a larger proximal inner diameter at the jejunal port 104, to a smaller distal inner diameter at the mating surface 113, and this can help to prevent leakage of liquid compositions from the GJ button 101, as the liquid compositions flow from jejunal channel 106 of the GJ button 101 to the jejunal tube passage 117 of the jejunal tube body 118. Without wishing to be bound by theory, it is believed that use of a ring 114 and mating surface 113 for mating the jejunal tube 115 and the GJ button 101, in combination with the funnel portion 116 between the jejunal port 104 and the mating surface 113, provides a structurally reliable and efficient solution for withstanding increases in pressure associated with the funneling of a liquid composition at the site of connection of the jejunal tube 115 and the GJ button 101, without leakage of the liquid composition or displacement of the jejunal tube 115.

Operative connection of the jejunal tube 115 and the GJ button 101 can be accomplished during assembly of the GJ feeding tube device 100, for example by sliding the jejunal tube 115 through jejunal channel 106 of the GJ button 101 distally, until the ring 114 of the jejunal tube 115 mates with the mating surface 113. A lubricant, such as isopropyl alcohol, can be used to facilitate the sliding.

Operative connection of the jejunal tube 115 and the GJ button 101 puts the jejunal channel 106 of the GJ button 101 and the jejunal tube passage 117 of the jejunal tube body 118 in fluid communication, allowing liquid compositions to flow therebetween and therethrough.

As shown in FIG. 9 and FIGS. 16-18, the ring 114 and the mating surface 113 can be shaped for a complementary fit. By this it is meant that the mating surface 113 can have a contour that matches the shape of the ring 114, along a proximal ring surface 144, a radial ring surface 145, and a distal ring surface 146 of the ring 114. For example, the mating surface 113 can have a contour that matches the shape of the ring 114 such that, upon mating of the ring 114 and the mating surface 113, the ring 114 is in contact with substantially all, e.g. 90%, 95%, or more, of the mating surface 113. Also for example, the mating surface 113 can have a contour that matches the shape of the ring 114 such that, upon mating of the ring 114 and the mating surface 113, the ring 114 is in contact with all of the mating surface 113.

With reference to FIG. 18, in some examples the ring 114 has an axial length 147, and the outer diameter 143 is substantially uniform along the axial length 147. By this it is meant that the ring 114 has an outer diameter 143 along the axial length 147 that varies, if at all, by less than 10%, e.g. by less than 5%, less than 2%, or less than 1%, along the axial length 147.

In some examples the axial length 147 of the ring 114 is 0.020 inches to 0.200 inches and the outer diameter 143 of the ring 114 is 0.080 inches to 0.180 inches. These are sizes that are well suited for mating of the ring 114 and the mating surface 113, and thus for securely joining the jejunal tube 115 and the GJ button 101. Thus, in some examples the axial length 147 of the ring 114 is 0.020 inches to 0.100 inches and the outer diameter 143 of the ring 114 is 0.080 inches to 0.130 inches. Also, in some examples the axial length 147 of the ring 114 is 0.020 inches to 0.060 inches and the outer diameter 143 of the ring 114 is 0.080 inches to 0.110 inches.

With reference to FIG. 9, FIGS. 16-18, and FIG. 24, the mating surface 113 can have an inner diameter 148 that is slightly smaller than the outer diameter 143 of the ring 114. This can provide a compression fit, allowing the radial compression of the ring 114 by the mating surface 113 to keep the jejunal tube 115 and the GJ button 101 securely joined. Thus, in some examples, the mating surface 113 has an inner diameter 148 that is 0.010 inches to 0.030 inches less than the outer diameter 143 of the ring 114. Also, in some examples the mating surface 113 has an inner diameter 148 that is 0.015 inches to 0.025 inches less than the outer diameter 143 of the ring 114. Also in some examples the mating surface 113 has an inner diameter 148 that is 0.020 inches less than the outer diameter 143 of the ring 114.

In some examples, the ring 114 has a substantially cylindrical shape.

As shown in FIG. 5 and FIGS. 9-11, the multi-lumen tube 119 and the GJ button 101 are operatively connected at the multi-lumen tube proximal end 121 and the base opening 109. For example, the multi-lumen tube 119 and the GJ button 101 can be operatively connected based on overmolding the multi-lumen tube 119 with the GJ button body 102. Also for example, the multi-lumen tube 119 and the GJ button 101 can be operatively connected based on other approaches, such as use of an adhesive.

Operative connection of the multi-lumen tube 119 and the GJ button 101 puts the gastric channel 105 of the GJ button 101 and the gastric lumen 123 of the multi-lumen tube 119 in fluid communication, allowing liquid compositions to flow therebetween and therethrough. Operative connection of the multi-lumen tube 119 and the GJ button 101 also aligns the jejunal channel 106 of the GJ button 101 with the jejunal lumen 124 of the multi-lumen tube 119.

Again with reference to FIG. 5 and FIGS. 9-11, the jejunal tube 115 extends through the jejunal lumen 124 of the multi-lumen tube 119. Following placement of the GJ feeding tube device 100 in a patient, the multi-lumen tube 119 thereby keeps the portion of the jejunal tube 115 located within the jejunal lumen 124 aligned with the gastric lumen 123 in the corresponding stoma and stomach of the patient.

As noted above, the jejunal tube body 118 has a size of French 8 or smaller. Similarly as for the mating surface 113 and the ring 114, the jejunal lumen 124 of the multi-lumen tube 119 can have an inner diameter that is slightly smaller than an outer diameter of the jejunal tube 115. This can provide a compression fit, allowing radial compression of the jejunal tube 115 by the multi-lumen tube 119 to keep the jejunal tube 115 and the multi-lumen tube 119 securely joined. Thus, in some examples, the jejunal lumen 124 has an inner diameter that is 0.010 inches to 0.030 inches less than an outer diameter of the jejunal tube 115. Also, in some examples the jejunal lumen 124 has an inner diameter that is 0.015 inches to 0.025 inches less than an outer diameter of the jejunal tube 115. Also in some examples the jejunal lumen 124 has an inner diameter that is 0.020 inches less than an outer diameter of the jejunal tube 115.

The GJ feeding tube device 100 can be placed in patients, e.g. infants and children, for GJ feeding.

With reference to FIG. 1, FIG. 9, and FIGS. 11-13, for gastric feeding, a liquid composition, e.g. a nutrient composition or a pharmaceutical composition, can be introduced via tubing and a connector into the GJ feeding tube device 100 through the gastric port 103 of the GJ button 101. The liquid composition can flow past the gastric port valve 110, and through the gastric channel 105. From there, the liquid composition can flow through the gastric lumen proximal opening 125 of the gastric lumen 123 of the multi-lumen tube body 120 of the multi-lumen tube 119. The liquid composition can flow through the gastric lumen 123. The liquid composition can exit the multi-lumen tube 119 via the gastric lumen distal opening 127, into the stomach of the patient.

With reference to FIG. 1, FIG. 9, FIGS. 11-14, FIG. 18, and FIG. 19, for jejunal feeding, a liquid composition, again e.g. a nutrient composition or a pharmaceutical composition, can be introduced via tubing and a connector into the GJ feeding tube device 100 through the jejunal port 104 of the GJ button 101. The liquid composition can flow past the jejunal port valve 111, and through the jejunal channel 106, including the funnel portion 116 thereof. From there, the liquid composition can flow through the proximal opening 134 of the jejunal tube passage 117 of the jejunal tube body 118 of the jejunal tube 115. The liquid composition can flow through the jejunal tube passage 117. The liquid composition can exit the jejunal tube 115 via the distal opening 135, into the small intestine of the patient.

In some examples, one or more of the jejunal tube 115 or the multi-lumen tube 119 further comprises barium sulfate. Barium sulfate is radiopaque, allowing a physician to easily view the placement by X-ray. Thus, in some examples, the jejunal tube 115 can comprise barium sulfate, e.g. within the jejunal tube body 118. Also in some examples, the multi-lumen tube 119 can further comprise barium sulfate, e.g. as a barium sulfate stripe positioned on the multi-lumen tube 119.

As shown in FIG. 1, FIG. 5, FIGS. 10-13, FIGS. 21-25, in some examples, the GJ feeding tube device 100 further comprises a balloon 149. In accordance with these examples, the GJ button 101 further comprises a balloon port 150 and a balloon channel 151, the multi-lumen tube 119 further comprises a balloon lumen 152, and the balloon 149 is attached to the multi-lumen tube 119, operatively connected to the balloon lumen 152, and reversibly inflatable for internal retention of the multi-lumen tube 119 in a patient.

Figure 11:
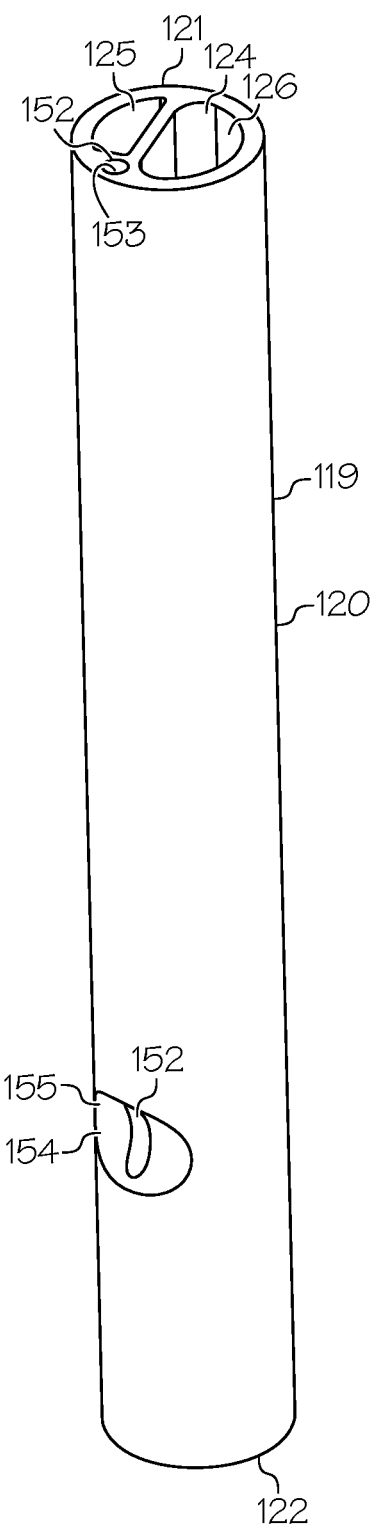
FIG. 11 is a perspective view of the multi-lumen tube of the GJ feeding tube device of FIG. 1, shown separately from the GJ feeding tube device.
Figure 12:
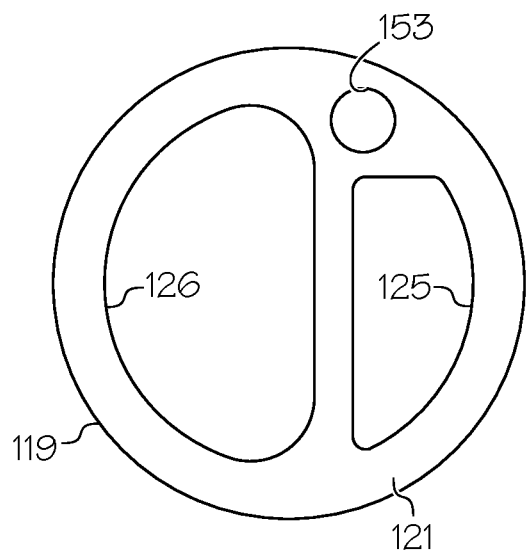
FIG. 12 is a top view of the multi-lumen tube of the GJ feeding tube device of FIG. 1, shown separately from the GJ feeding tube device.
Figure 13:
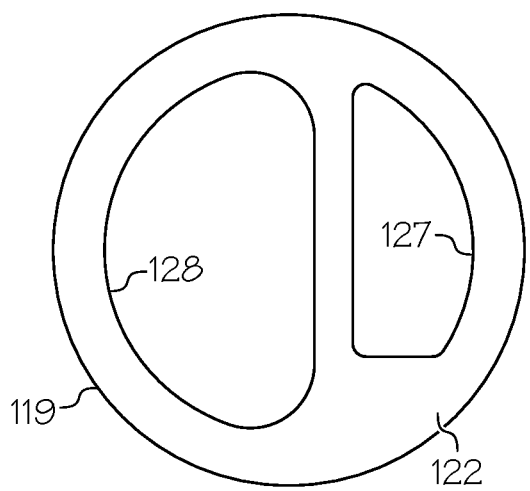
FIG. 13 is a bottom view of a multi-lumen tube of the GJ feeding tube device of FIG. 1, shown separately from the GJ feeding tube device.
Figure 14:
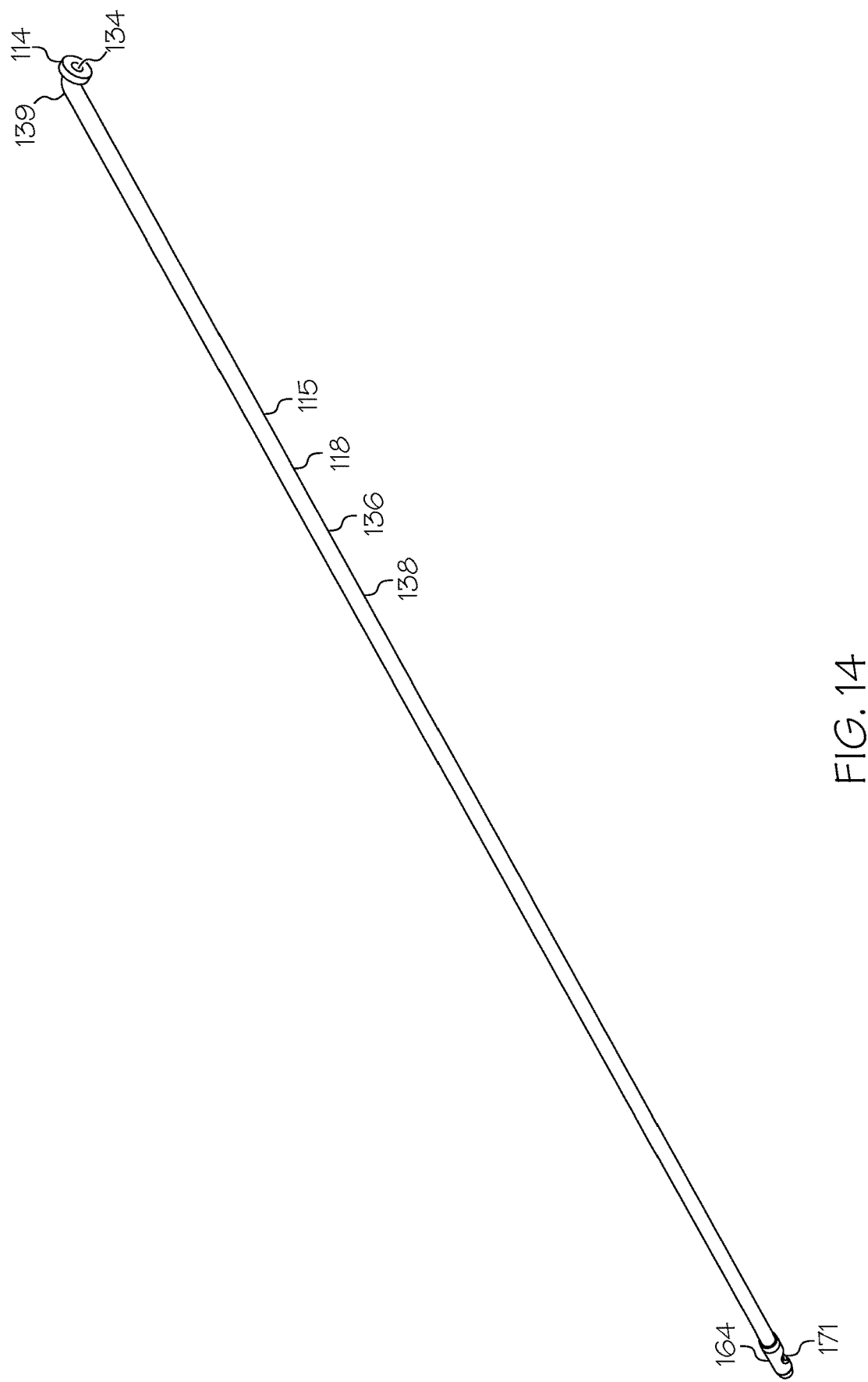
FIG. 14 is a perspective view of the jejunal tube of the GJ feeding tube device of FIG. 1, shown separately from the GJ feeding tube device.
Figure 15:
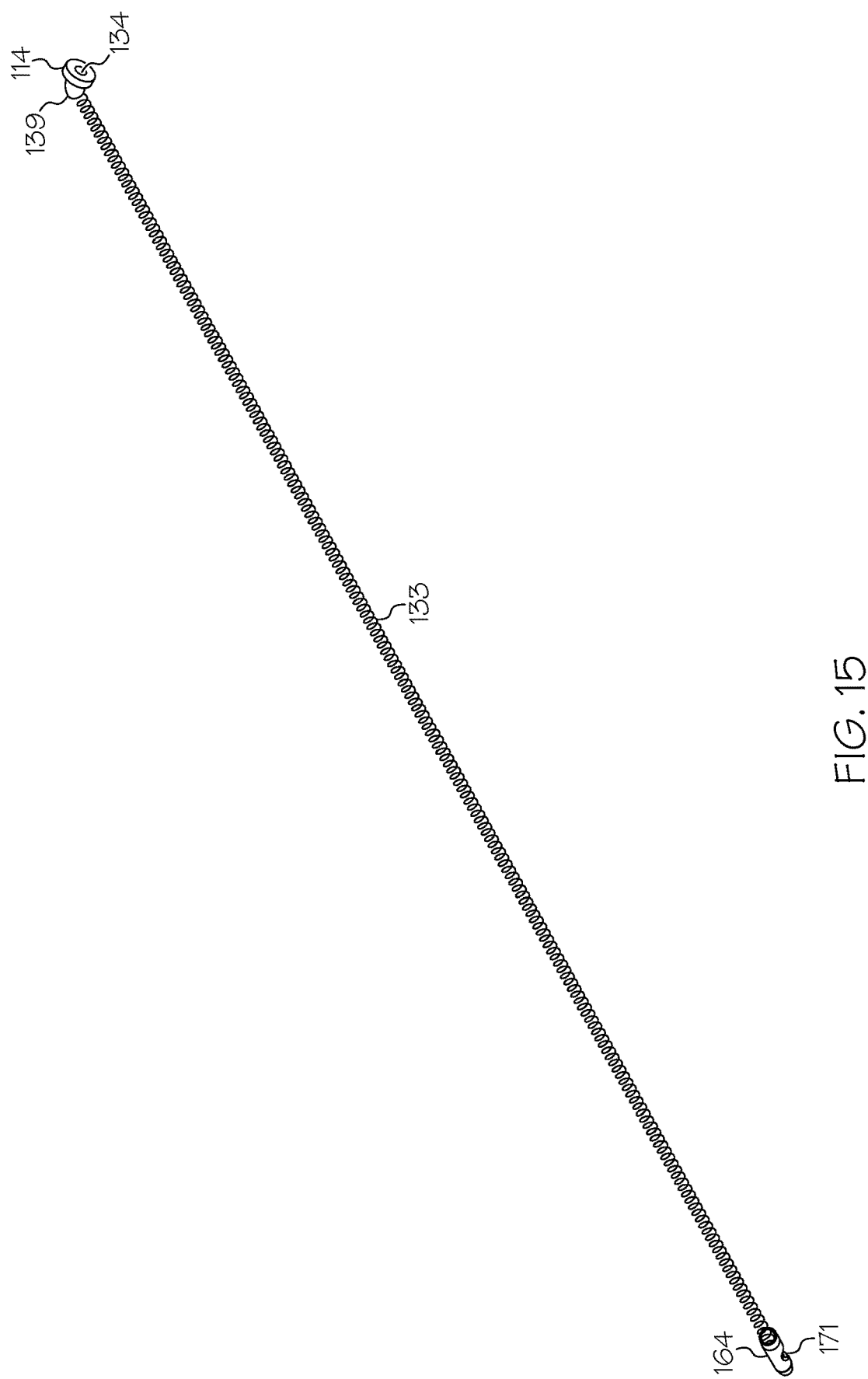
FIG. 15 is a partial offset sectional view of the jejunal tube of FIG. 14, showing a spring embedded within the jejunal tube.
Figure 16:
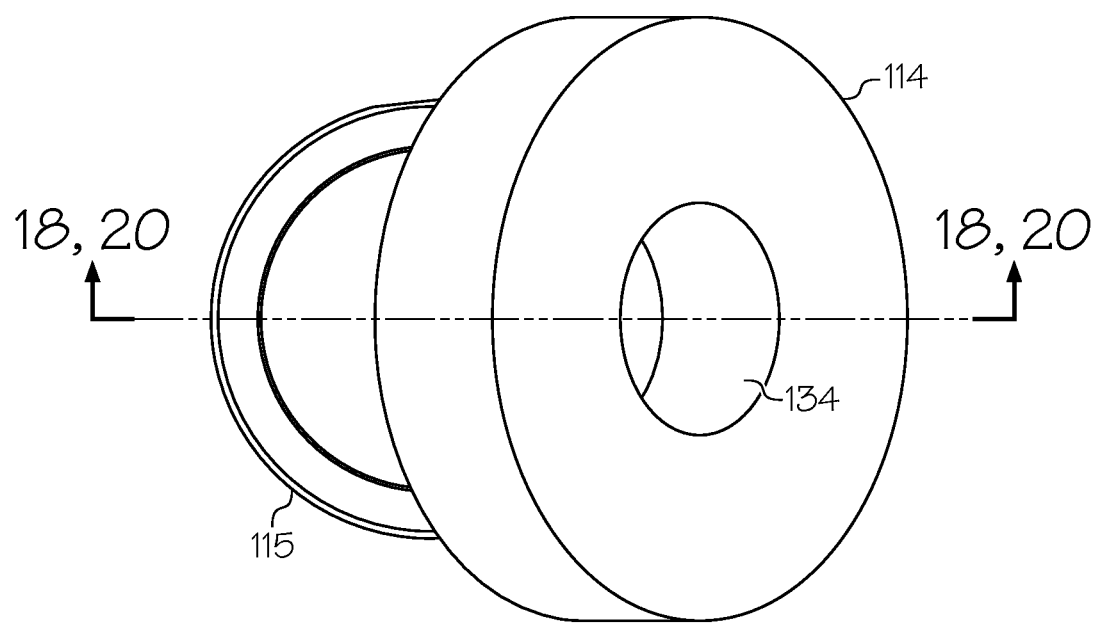
FIG. 16 is a top view of the jejunal tube of the GJ feeding tube device of FIG. 1, shown separately from the GJ feeding tube device.

With reference to FIGS. 11-13, the balloon lumen 152 can have a balloon lumen proximal opening 153 located at the multi-lumen tube proximal end 121 and a balloon lumen distal opening 154 located along the multi-lumen tube body 120. The balloon lumen 152 can be formed, for example, by forming a third lumen during extrusion of the multi-lumen tube body 120, including a proximal opening and a distal opening at the multi-lumen tube proximal end 121 and the multi-lumen tube distal end 122, respectively. The distal opening of the third lumen can be backfilled. A nick 155 can be made along the multi-lumen tube body 120, extending from the surface of the multi-lumen tube body 120 to the third lumen. This results in the balloon lumen 152 having a balloon lumen proximal opening 153 located at the multi-lumen tube proximal end 121, i.e. the proximal opening of the third lumen, and a balloon lumen distal opening 154 located along the multi-lumen tube body 120, i.e. the nick 155.

Figure 21:
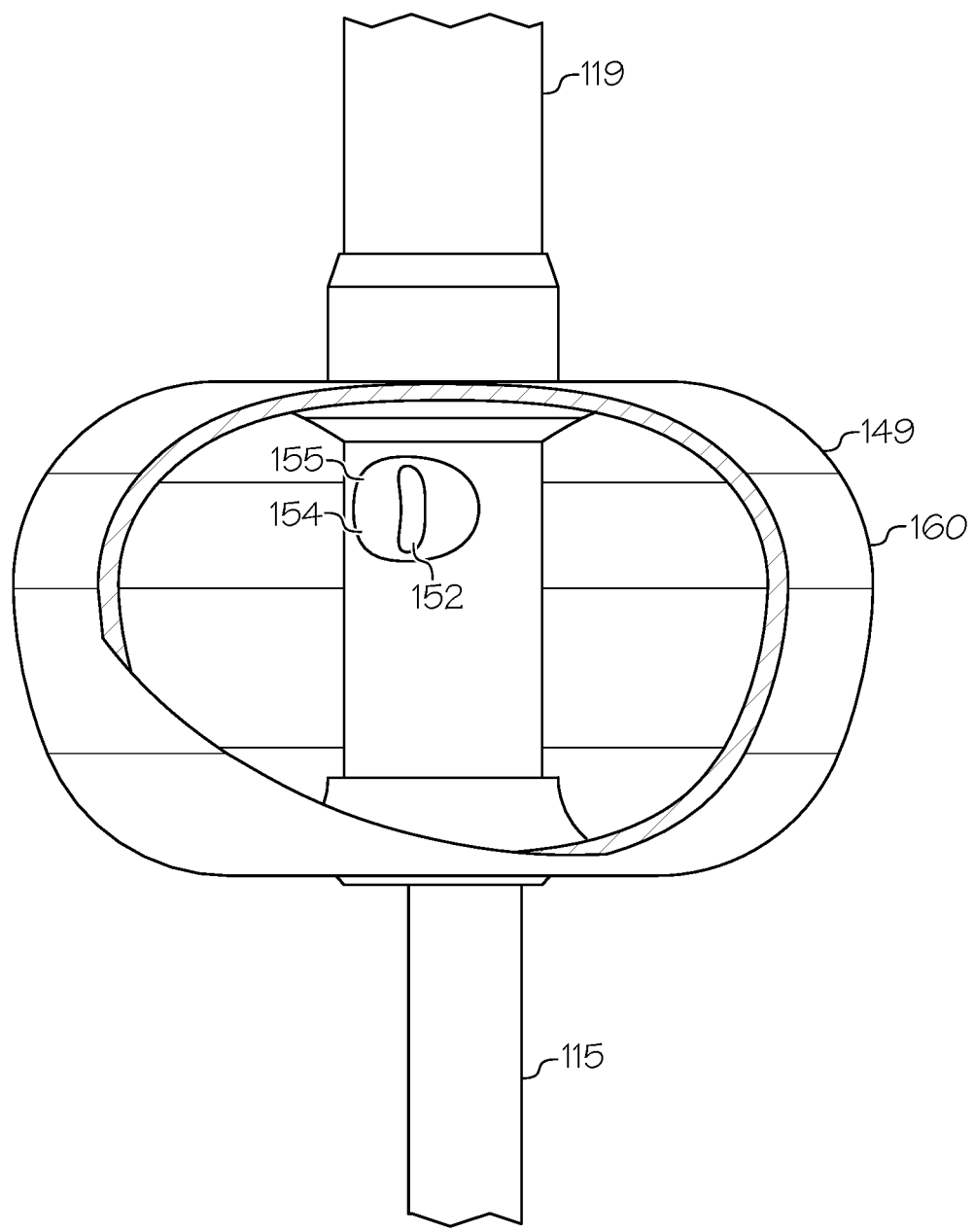
FIG. 21 is an enlarged view of a part of the multi-lumen tube and a part of the balloon of the GJ feeding tube device of FIG. 1, the balloon being shown in partial sectional view, to illustrate positioning of the balloon lumen distal opening of the multi-lumen tube with respect to the balloon.
Figure 22:
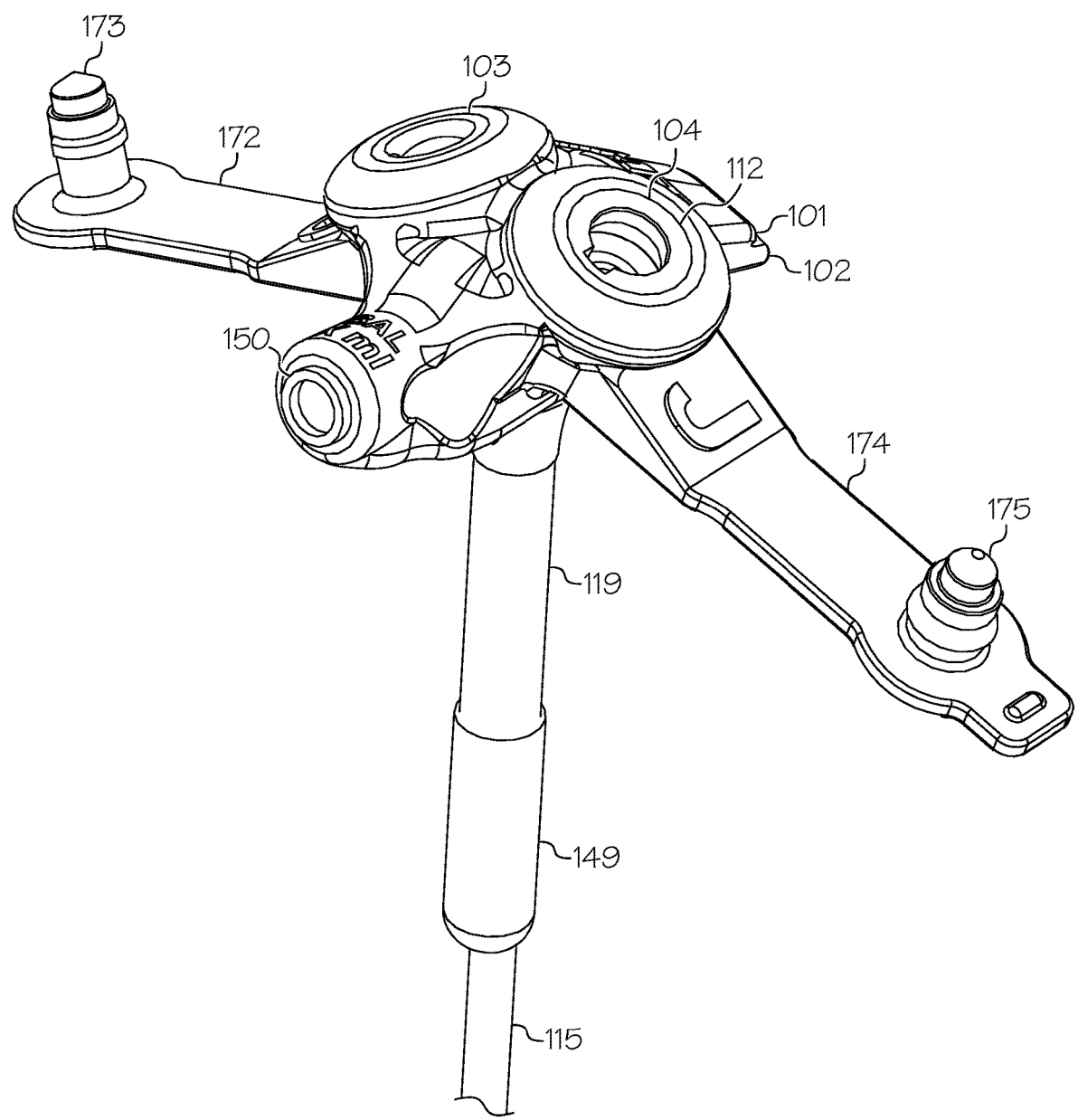
FIG. 22 is an enlarged perspective view of the GJ button, the multi-lumen tube, and the balloon of the GJ feeding tube device of FIG. 1, the balloon being deflated.
Figure 23:
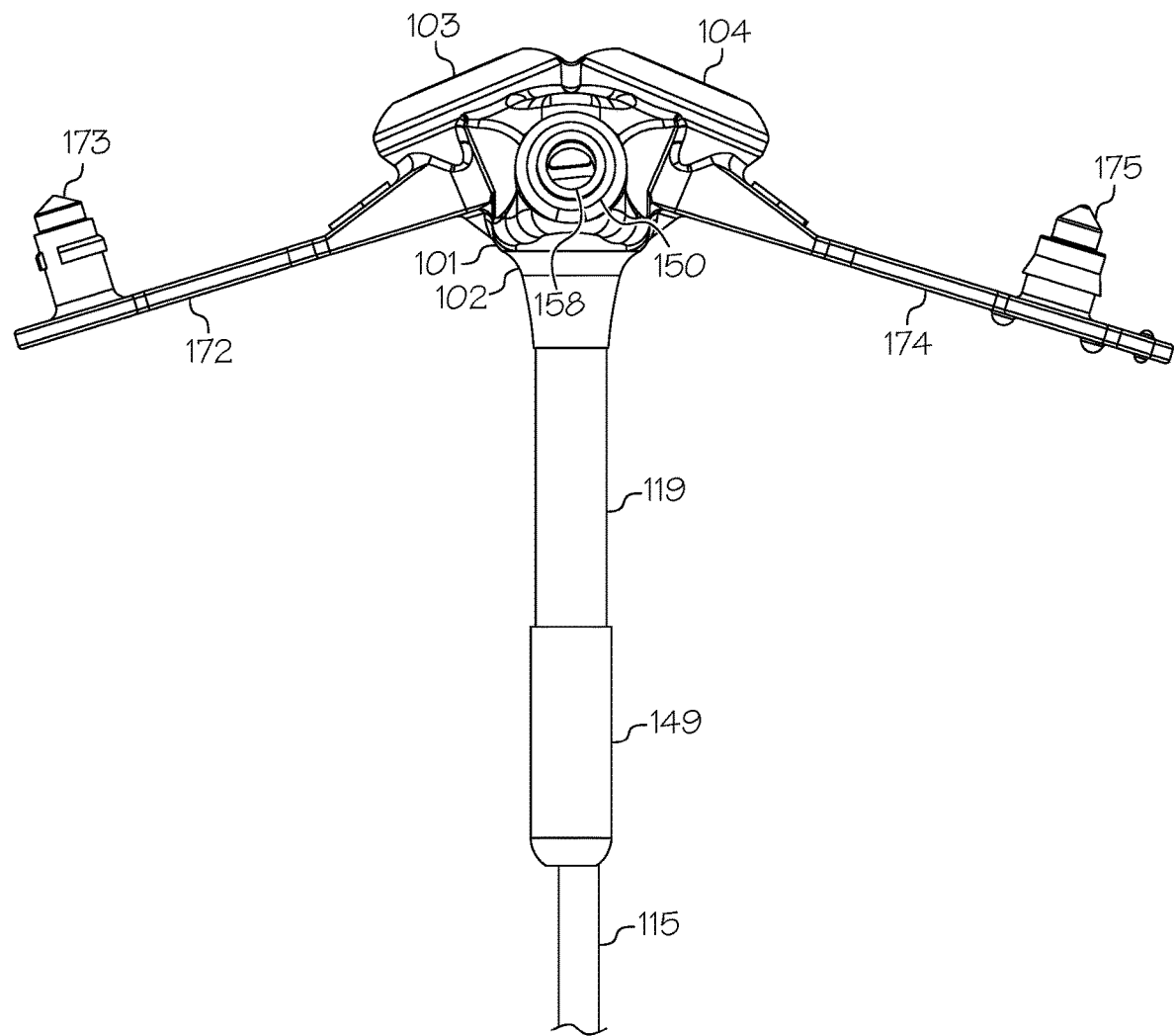
FIG. 23 is an enlarged first side view of the GJ button, the multi-lumen tube, and the balloon of the GJ feeding tube device of FIG. 1, the balloon being deflated.
Figure 25:
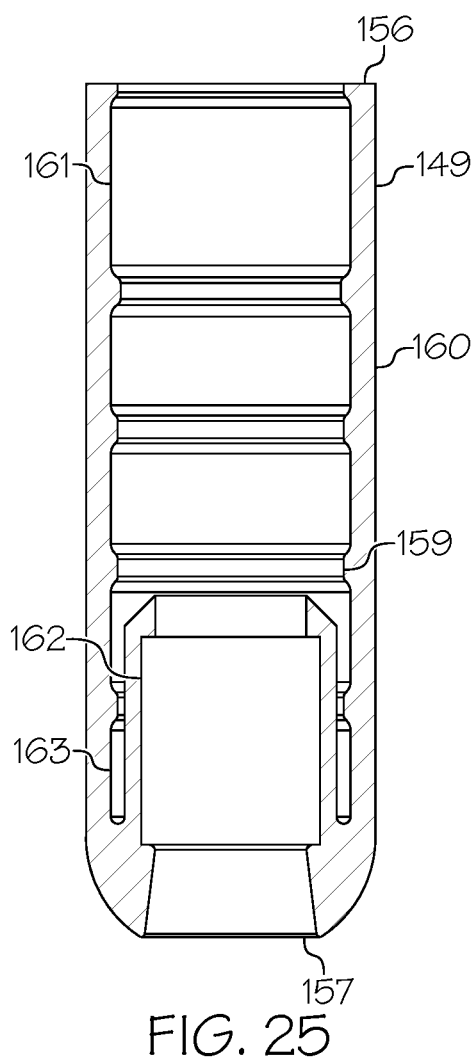
FIG. 25 is a view of the balloon of the jejunal tube of the GJ feeding tube device of FIG. 1, shown separately from the GJ feeding tube device, the balloon being deflated.
Figure 26:
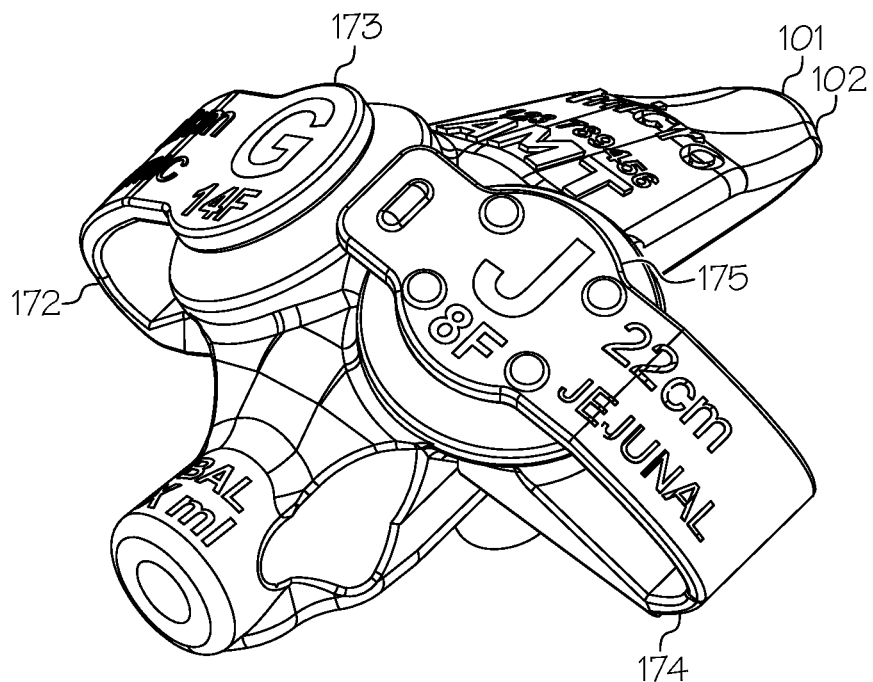
FIG. 26 is a perspective view of the GJ button of the GJ feeding tube device of FIG. 1, shown separately from the GJ feeding tube device, with the gastric port plug and the jejunal port plug inserted in the GJ button at the gastric port and the jejunal port, respectively.

With reference to FIG. 9, FIG. 21, and FIG. 25, the balloon 149 can be attached to the multi-lumen tube 119, for example, by use of adhesives, e.g. at or near a balloon proximal end 156 and a balloon distal end 157 of the balloon 149 that are in contact with the multi-lumen tube body 120, among other approaches. For example, the balloon 149 can have a hollow and generally cylindrical form, such that the balloon 149 can fit over the multi-lumen tube body 120, at the multi-lumen tube distal end 122, and be adhered there.

This can accomplish sealing of the balloon 149 to the multi-lumen tube body 120. The balloon 149 can be operatively connected to the balloon lumen 152 by positioning the balloon 149 over the balloon lumen distal opening 154, e.g. the nick 155, so that the balloon lumen 152 is in fluid communication with surfaces of the balloon 149 sealed to the multi-lumen tube body 120.

With reference to FIG. 5, FIG. 9, FIGS. 11-13, FIG. 21, FIG. 22, and FIG. 25, once operatively connected, the balloon 149 can be reversibly inflated for internal retention of the multi-lumen tube 119 in a patient, e.g. an infant or child. For example, a fluid, such as water or air, can be injected into the balloon port 150, from which it can flow through the balloon channel 151, into the balloon lumen 152 at the balloon lumen proximal opening 153, out from the balloon lumen 152 at the balloon lumen distal opening 154, and into the balloon 149. The balloon port 150 can include a balloon port valve 158, e.g. a check-valve, to allow control of flow of the fluid. In this way, the GJ feeding tube device 100 can be placed in a patient, e.g. an infant or child, through an incision in the abdominal wall, while the balloon 149 is deflated, e.g. while the deflated balloon 149 has a diameter that is sufficiently small to allow the multi-lumen tube 119 including the balloon 149 attached thereto to pass through the incision. Following placement, the balloon 149 can be inflated, e.g. by injection of fluid, with the balloon port valve 158 allowing the fluid to flow to the balloon 149 under pressure, but preventing backflow from the balloon 149. Once inflated, the balloon 149 promotes retention of the multi-lumen tube 119 in the infant or child, e.g. based on the inflated balloon 149 having a diameter sufficiently large to prevent the multi-lumen tube 119 including the balloon 149 attached thereto to pass through the incision. The GJ feeding tube device 100 can ultimately be removed by operating the balloon port valve 158 to release the fluid from the balloon 149 through the balloon port 150, thereby deflating the balloon 149, then removing the GJ feeding tube device 100 from the patient through the incision.

Again with reference to FIG. 5, FIG. 9, FIGS. 11-13, FIG. 21, FIG. 22, and FIG. 25, in some examples the balloon 149 comprises an inner membrane 159 and an outer membrane 160. The inner membrane 159 is adhered to the multi-lumen tube 119 at a first position 161 and a second position 162 of the inner membrane 159 near the balloon proximal end 156 and the balloon distal end 157, respectively, of the balloon 149. The balloon 149 includes a narrow space 163 between the adhered inner membrane 159 and the outer membrane 160 into which a fluid can flow during inflation. The balloon 149 is attached to the multi-lumen tube 119, at the multi-lumen tube distal end 122, based on fitting over the multi-lumen tube body 120, and partially extending distally therefrom. In accordance with these examples, when the balloon 149 is deflated, the balloon 149 flexes beyond the multi-lumen tube distal end 122, preventing contact between the multi-lumen tube distal end 122 and tissue of a patient during placement in the patient. Also in accordance with these examples, when the balloon 149 is inflated, fluid flows into the narrow space 163, causing the balloon 149 to inflate about the multi-lumen tube distal end 122, such that the multi-lumen tube distal end 122 is recessed with respect to the balloon 149, thereby preventing contact between the multi-lumen tube distal end 122 and tissue of the patient during use in the patient. Without wishing to be bound by theory, it is believed that this configuration provides a compact and reliable approach for protecting patient tissue from being damaged by contact with the multi-lumen tube distal end 122 without having to smooth, round, or otherwise finish the multi-lumen tube distal end 122.

As shown in FIG. 3, FIG. 4, FIG. 19, and FIG. 20, in some examples the GJ feeding tube device 100 further comprises a jejunal tip 164 attached at the jejunal tube distal end 132. The jejunal tip 164 can include a jejunal tip proximal end 165, a jejunal tip distal end 166, and a jejunal tip body 167 therebetween. The jejunal tip body 167 can define a jejunal tip passage 168 having a jejunal tip proximal opening 169 at the jejunal tip proximal end 165 and a jejunal tip distal opening 170 at the jejunal tip distal end 166. The jejunal tip 164 can be operatively connected to the jejunal tube 115 at the jejunal tube distal end 132 by sliding the jejunal tube distal end 132 into the jejunal tip proximal opening 169, with attachment, for example, by use of adhesive. In some examples the jejunal tip 164 also can have a lateral opening 171, e.g. positioned centrally between the jejunal tip proximal end 165 and the jejunal tip distal end 166.

The jejunal tip 164 can be a soft, atraumatic tip. This can allow for gentle navigation in the small intestine of a patient, e.g. an infant or child.

The jejunal tip 164 also can be radiopaque, e.g. based on including barium sulfate, again allowing a physician to easily view the placement by X-ray.

The jejunal tip 164 can comprise one or more of silicone or polyurethane, among other materials. In some examples, the jejunal tip 164 is made from silicone, e.g. 90%, 95%, 99%, or 100% of the material of the jejunal tip is silicone. In some examples, the jejunal tip 164 is made from polyurethane, e.g. 90%, 95%, 99%, or 100% of the material of the jejunal tip 164 is polyurethane.

In accordance with these examples, jejunal feeding can be carried out similarly as described above, except that the liquid composition can exit the jejunal tube 115 via the distal opening 135, into the jejunal tip passage 168 of the jejunal tip 164. The liquid composition can flow through the jejunal tip passage 168. The liquid composition can exit the jejunal tip 164, via the lateral opening 171 and/or the jejunal tip distal opening 170, into the small intestine of the patient.

With reference to FIG. 1, FIG. 5, FIG. 26, and FIG. 27, in some examples, the GJ button further comprises a gastric port strap 172 comprising a gastric port plug 173 and/or a jejunal port strap 174 comprising a jejunal port plug 175. The gastric port strap 172 can be flexible, allowing the gastric port plug 173 to be positioned adjacent the gastric port 103. The gastric port plug 173 can be used to reversibly close the gastric port 103, e.g. during periods when gastric feeding is not being carried out. This can be accomplished, for example, by removing a connector for feeding from the gastric port 103, and inserting the gastric port plug 173 into the GJ button 101 at the gastric port 103. To resume feeding, the gastric port plug 173 can be removed from the GJ button 101, and the connector can be attached to the gastric port 103. The jejunal port strap 174 and the jejunal port plug 175 can be used similarly to reversibly close the jejunal port 104, e.g. during periods when jejunal feeding is not being carried out.

Figure 6:
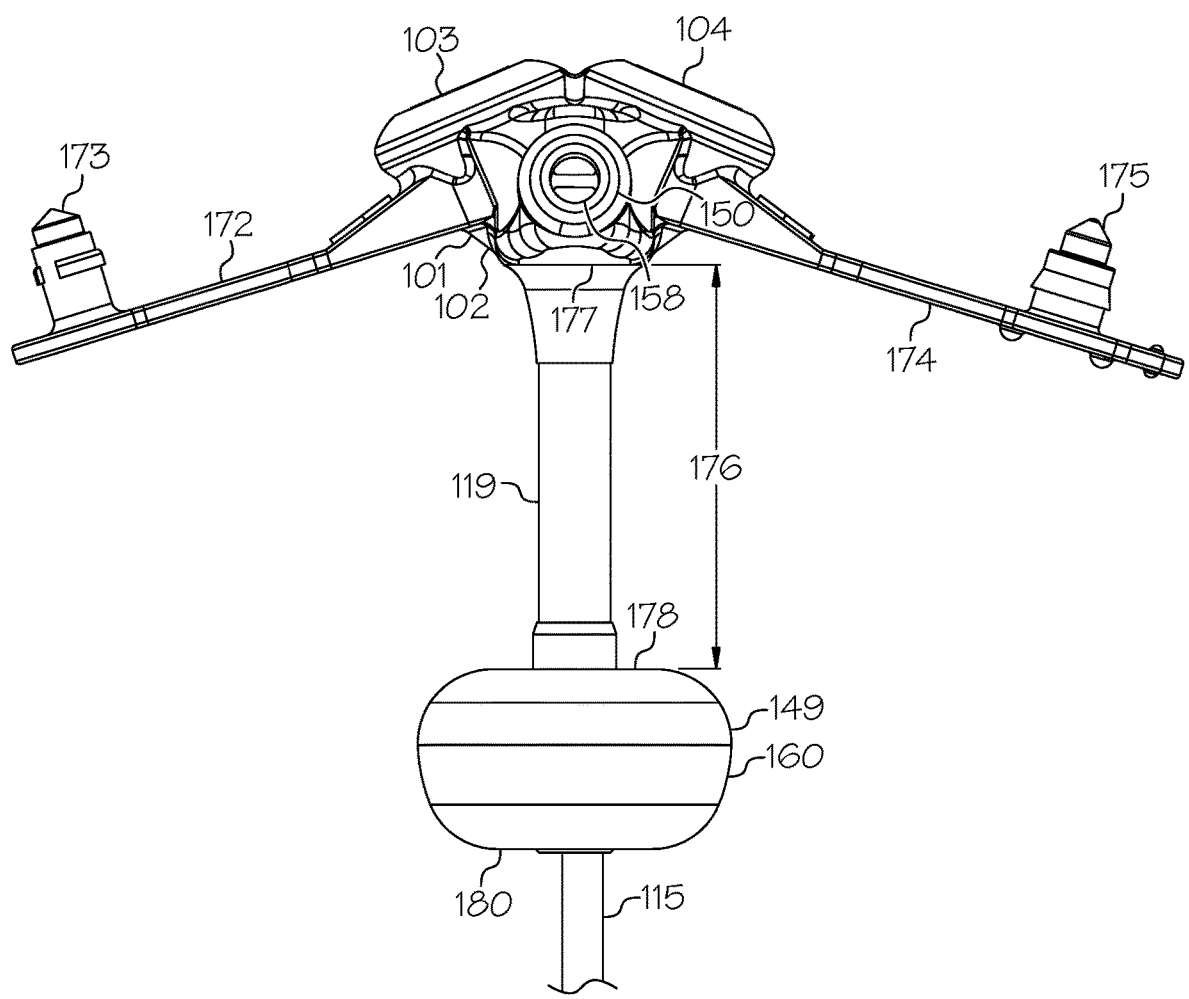
FIG. 6 is an enlarged first side view of the GJ button, the multi-lumen tube, and the balloon of the GJ feeding tube device of FIG. 1.
Figure 7:
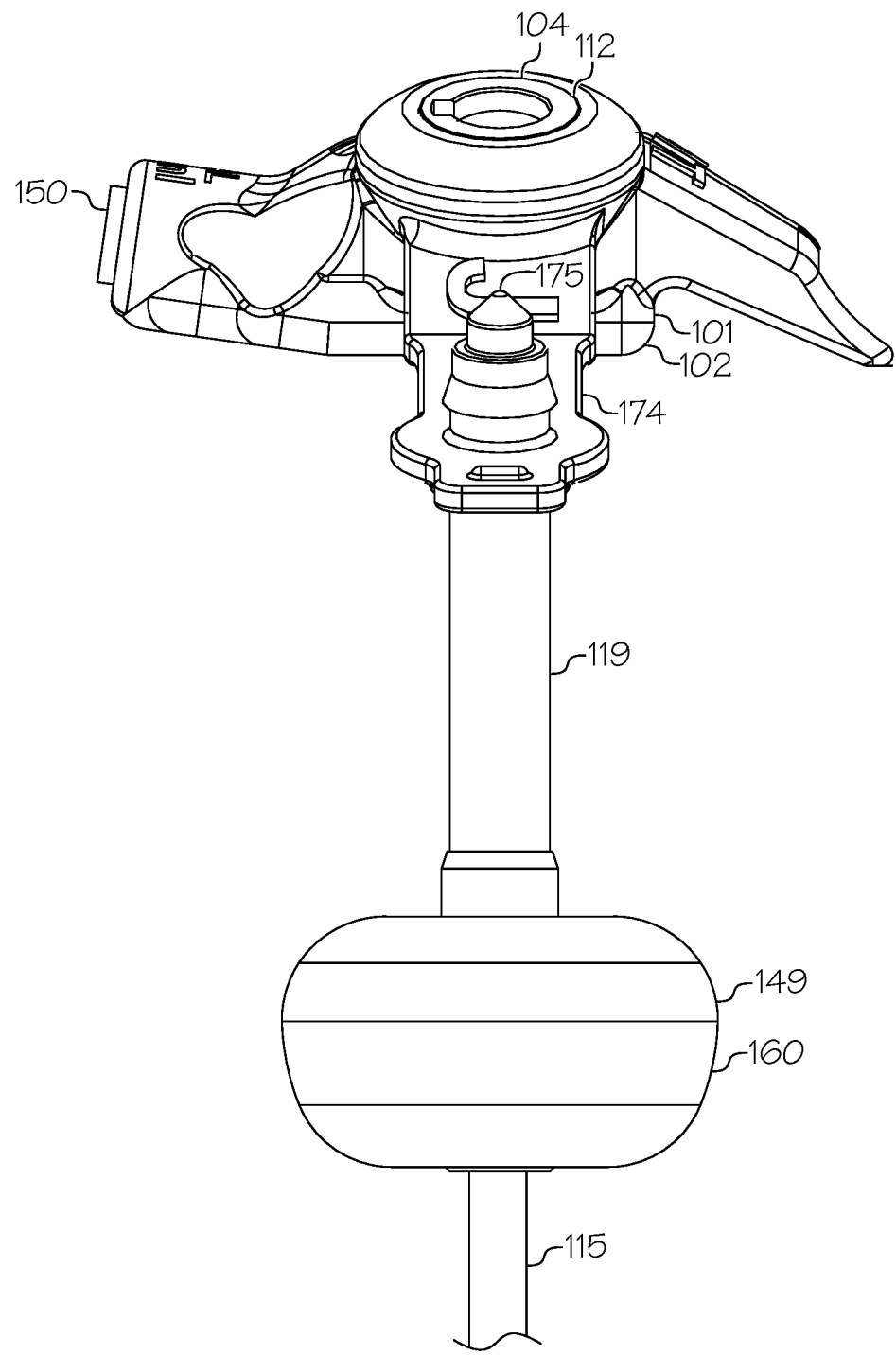
FIG. 7 is an enlarged second side view of the GJ button, the multi-lumen tube, and the balloon of the GJ feeding tube device of FIG. 1.
Figure 8:
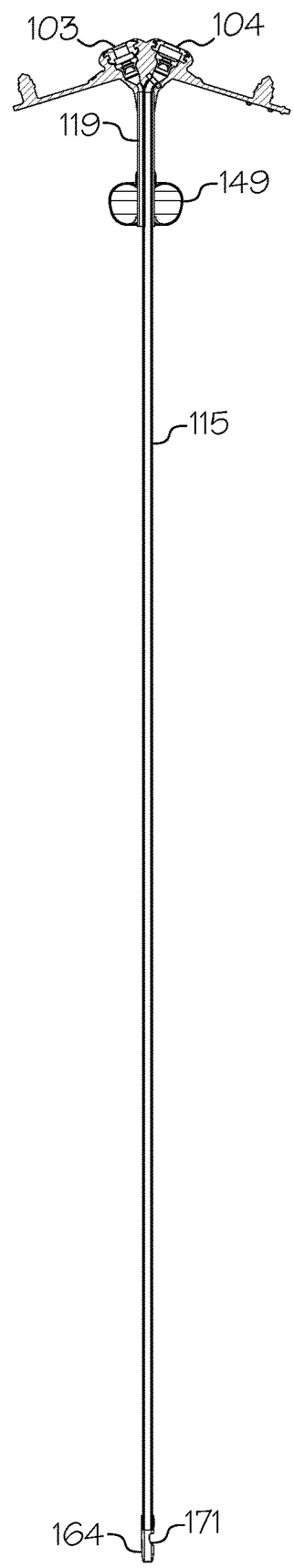
FIG. 8 is a sectional view of the GJ feeding tube device of FIG. 1.

With reference to FIG. 3 and FIG. 6, in some examples, the GJ feeding tube device 100 has a stoma length 176 of 0.5 cm to 6.0 cm. In accordance with these examples, the GJ feeding tube device 100 can comprise a balloon 149, the GJ button 101 can have a GJ button base contact surface 177, corresponding to a part of the GJ button 101 in contact with skin of a patient following placement, and the balloon 149 can have a balloon expanded portion proximal end 178, corresponding to the proximal end of the expanded portion of the balloon 149. In accordance with these examples, a stoma length 176 of 0.5 cm to 6.0 cm means a length of 0.5 cm to 6.0 cm as measured from the GJ button base contact surface 177 of the GJ button 101 to the balloon expanded portion proximal end 178 of the balloon 149. Thus, in some examples the GJ feeding tube device 100 has a stoma length 176 of 0.5 cm to 1.0 cm. Also, in some examples the GJ feeding tube device 100 has a stoma length 176 of 0.5 cm to 0.9 cm, 0.5 cm to 0.8 cm, 0.5 cm to 0.7 cm, or 0.5 cm to 0.6 cm.

Figure 5:
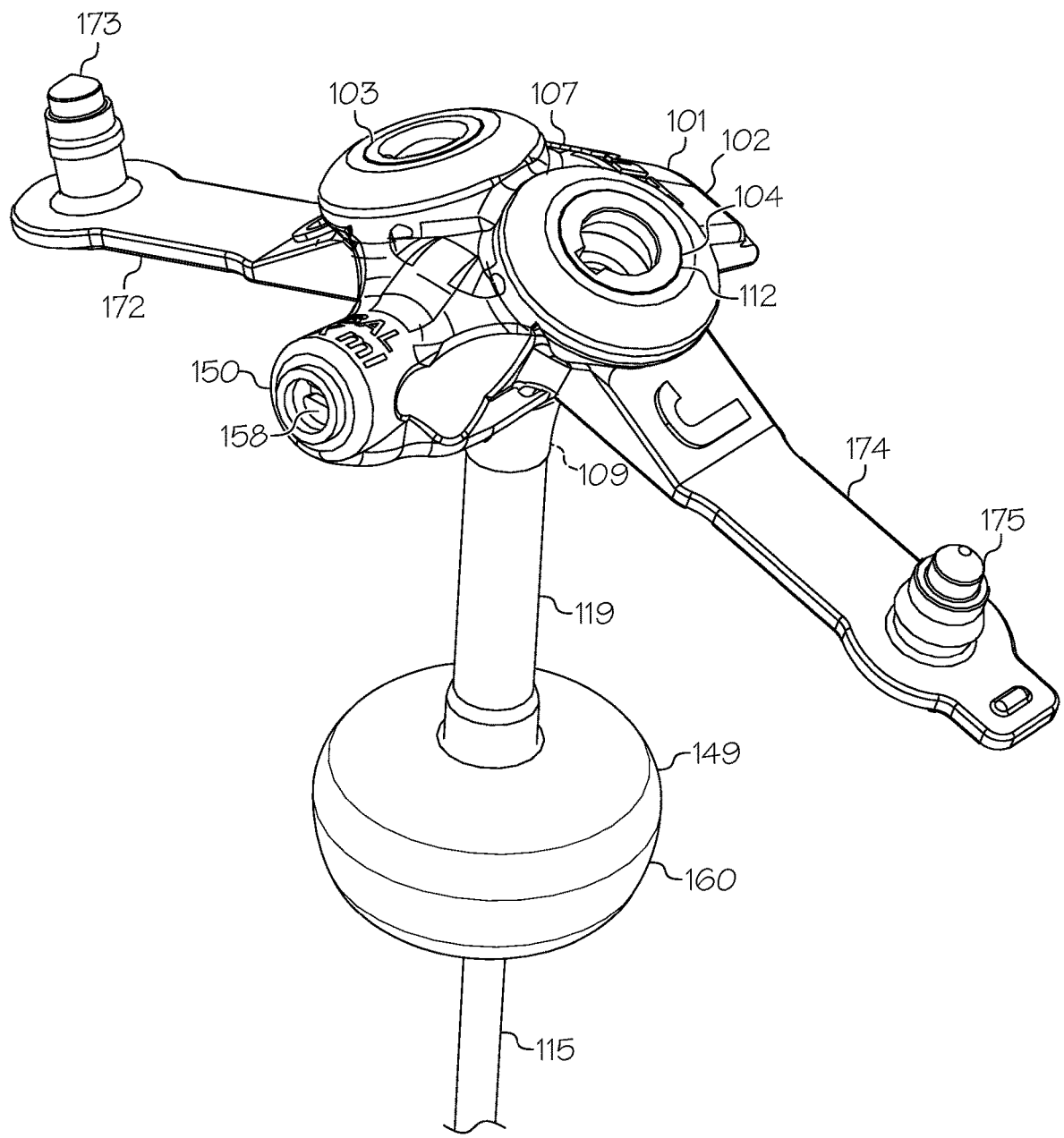
FIG. 5 is an enlarged perspective view of the GJ button, the multi-lumen tube, and the balloon of the GJ feeding tube device of FIG. 1.
Figure 19:
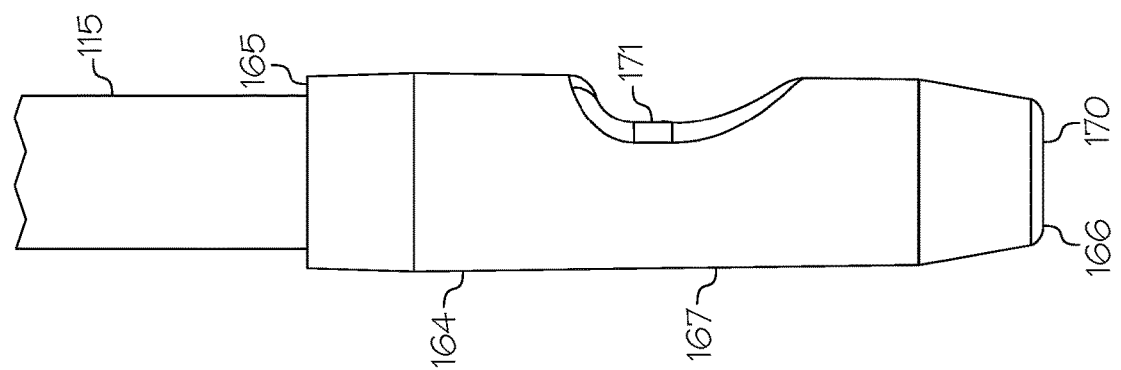
FIG. 19 is an enlarged first side view of a distal portion of the jejunal tube of the GJ feeding tube device of FIG. 1, shown separately from the GJ feeding tube device.

With reference to FIG. 3, FIG. 5, and FIG. 19, in some examples, the GJ feeding tube device 100 has a jejunal length 179 of 10 cm to 60 cm. In accordance with these examples, the GJ feeding tube device 100 can comprise a balloon 149, and the balloon 149 can comprise balloon expanded portion distal end 180, corresponding to the distal end of an expanded portion of the balloon 149. In accordance with these examples, a jejunal length 179 of 10 cm to 60 cm means a length of 10 cm to 60 cm from a balloon expanded portion distal end 180 of the balloon 149 to a jejunal tip proximal end 165 of a jejunal tip 164 (i.e. not including the jejunal tip 164). Thus, in some examples the GJ feeding tube device 100 has a jejunal length 179 of 10 cm to 15 cm. Also, in some examples the GJ feeding tube device 100 has a jejunal length 179 of 10 cm to 14 cm, 10 cm to 13 cm, 10 cm to 12 cm, or 10 cm to 11 cm.

While this invention has been described in conjunction with the specific embodiments outlined above, it is evident that many alternatives, modifications and variations will be apparent to those skilled in the art. Accordingly, the preferred embodiments of the invention as set forth above are intended to be illustrative, not limiting. Various changes may be made without departing from the spirit and scope of the invention.

What is claimed is:

1. A gastric jejunal (GJ) feeding tube device for GJ feeding of an infant or child, comprising:
   (a) a GJ button comprising (i) a GJ button body, (ii) a gastric port, (iii) a jejunal port, (iv) a gastric channel, and (v) a jejunal channel, the GJ button body having a proximal surface, a distal surface, and a base opening, the gastric port and the jejunal port being positioned at the proximal surface, the base opening being positioned at the distal surface, the gastric channel and the jejunal channel extending from the gastric port and the jejunal port, respectively, to the base opening, and the jejunal channel having a mating surface therein;
   (b) a multi-lumen tube comprising (i) a multi-lumen tube body, (ii) a multi-lumen tube proximal end, and (iii) a multi-lumen tube distal end, the multi-lumen tube body defining a gastric lumen and a jejunal lumen, the gastric lumen and the jejunal lumen each having a proximal opening located at the multi-lumen tube proximal end and a distal opening located along the multi-lumen tube body or at the multi-lumen tube distal end; and
   (c) a jejunal tube comprising (i) a jejunal tube body, (ii) a jejunal tube proximal end, (iii) a jejunal tube distal end, (iv) a spring, and (v) a ring, the jejunal tube body defining a jejunal tube passage having a proximal opening located at the jejunal tube proximal end and a distal opening located at the jejunal tube distal end, the spring being positioned within the jejunal tube body, extending therealong, and providing a kink-resistant feature thereto, and the ring being positioned at the jejunal tube proximal end, coaxially with respect to the jejunal tube body, wherein:
   the jejunal tube and the GJ button are operatively connected at the ring and the mating surface, the mating surface radially compressing the ring;
   the multi-lumen tube and the GJ button are operatively connected at the multi-lumen tube proximal end and the base opening;
   the jejunal tube extends through the jejunal lumen of the multi-lumen tube;
   the ring has a higher durometer than the jejunal tube body; and
   the ring has an outer diameter that does not substantially decrease distally with respect to the jejunal tube.

2. The GJ feeding tube device of claim 1, wherein the ring and the mating surface are shaped for a complementary fit.

3. The GJ feeding tube device of claim 1, wherein the ring has an axial length, and the outer diameter is substantially uniform along the axial length.

4. The GJ feeding tube device of claim 3, wherein the axial length of the ring is 0.020 inches to 0.200 inches and the outer diameter of the ring is 0.080 inches to 0.180 inches.

5. The GJ feeding tube device of claim 3, wherein the mating surface has an inner diameter that is 0.010 inches to 0.030 inches less than the outer diameter of the ring.

6. The GJ feeding tube device of claim 1, wherein the ring has a substantially cylindrical shape.

7. The GJ feeding tube device of claim 1, wherein the jejunal channel further comprises a funnel portion between the jejunal port and the mating surface, the funnel portion having an inner diameter that decreases distally.

8. The GJ feeding tube device of claim 1, wherein the ring is positioned at the jejunal tube proximal end based on overmolding the jejunal tube body with the ring.

9. The GJ feeding tube device of claim 1, wherein the jejunal tube body comprises a jejunal tube body wall, the spring being embedded in the jejunal tube body wall.

10. The GJ feeding tube device of claim 1, wherein the jejunal tube body has a size of French 8 or smaller.

11. The GJ feeding tube device of claim 1, wherein the multi-lumen tube body has a size of French 14 or smaller.

12. The GJ feeding tube device of claim 1, wherein the gastric lumen of the multi-lumen tube has a gastric lumen length, the jejunal lumen of the multi-lumen tube has a jejunal lumen length, and the gastric lumen length is about the same as the jejunal lumen length.

13. The GJ feeding tube device of claim 1, wherein one or more of the jejunal tube or the multi-lumen tube further comprises barium sulfate.

14. The GJ feeding tube device of claim 1, wherein the multi-lumen tube and the GJ button are operatively connected based on overmolding the multi-lumen tube with the GJ button body.

15. The GJ feeding tube device of claim 1, further comprising a balloon, wherein:
   (i) the GJ button further comprises a balloon port and a balloon channel;
   (ii) the multi-lumen tube further comprises a balloon lumen; and
   (iii) the balloon is attached to the multi-lumen tube, operatively connected to the balloon lumen, and reversibly inflatable for internal retention of the multi-lumen tube in a patient.

16. The GJ feeding tube device of claim 15, wherein the GJ feeding tube device has a stoma length of 0.5 cm to 6.0 cm.

17. The GJ feeding tube device of claim 15, further comprising a jejunal tip attached at the jejunal tube distal end.

18. The GJ feeding tube device of claim 17, wherein the GJ feeding tube device has a jejunal length of 10 cm to 60 cm.

19. The GJ feeding tube device of claim 1, further comprising a jejunal tip attached at the jejunal tube distal end.

20. The GJ feeding tube device of claim 1, wherein the GJ button body comprises one or more of silicone or polyurethane.

21. The GJ feeding tube device of claim 1, wherein the multi-lumen tube body comprises one or more of silicone or polyurethane.

22. The GJ feeding tube device of claim 1, wherein the jejunal tube body comprises one or more of polyurethane or silicone.

23. The GJ feeding tube device of claim 1, wherein the spring comprises one or more of polyether ether ketone, stainless steel, nylon, or high density polyethylene.

24. The GJ feeding tube device of claim 1, wherein the ring comprises one or more of polyurethane or high-durometer silicone.

25. The GJ feeding tube device of claim 1, wherein the ring has a filled toroidal structure about the proximal opening of the jejunal tube passage of the jejunal tube body.

* * * * *